United States Patent
Kontschieder et al.

(10) Patent No.: US 10,776,423 B2
(45) Date of Patent: Sep. 15, 2020

(54) MOTOR TASK ANALYSIS SYSTEM AND METHOD

(71) Applicant: NOVARTIS AG, Basel (CH)

(72) Inventors: Peter Kontschieder, Cambridge (GB); Jonas Dorn, Basel (CH); Darko Zikic, Cambridge (GB); Antonio Criminsi, Cambridge (GB); Frank Kurt Dahlke, Basel (CH)

(73) Assignee: Novartis AG, Basel (CH)

( * ) Notice: Subject to any disclaimer, the term of this patent is extended or adjusted under 35 U.S.C. 154(b) by 270 days.

(21) Appl. No.: 15/508,618

(22) PCT Filed: Sep. 3, 2015

(86) PCT No.: PCT/IB2015/056719
§ 371 (c)(1),
(2) Date: Mar. 3, 2017

(87) PCT Pub. No.: WO2016/038516
PCT Pub. Date: Mar. 17, 2016

(65) Prior Publication Data
US 2017/0293805 A1    Oct. 12, 2017

Related U.S. Application Data

(60) Provisional application No. 62/048,132, filed on Sep. 9, 2014.

(51) Int. Cl.
*G06K 9/00* (2006.01)
*G06F 16/783* (2019.01)
(Continued)

(52) U.S. Cl.
CPC ........ *G06F 16/783* (2019.01); *G06F 16/9566* (2019.01); *G06K 9/00342* (2013.01);
(Continued)

(58) Field of Classification Search
CPC ........... G06K 9/00744; G06K 9/00342; G06K 9/6278; G06K 9/6267; G06K 2009/00738;
(Continued)

(56) References Cited

U.S. PATENT DOCUMENTS 7,643,655 B2 * 1/2010 Liang ................. G06K 9/00362
                                                    119/421
8,189,866 B1 * 5/2012 Gu ..................... G06K 9/00335
                                                    348/169
(Continued)

FOREIGN PATENT DOCUMENTS

WO     2001/88836 A1     11/2001
WO     2007/020568 A2    2/2007
(Continued)

OTHER PUBLICATIONS

Martínez, Fabio, Antoine Manzanera, and Eduardo Romero. "A motion descriptor based on statistics of optical flow orientations for action classification in video-surveillance." In Multimedia and Signal Processing, pp. 267-274. Springer Berlin Heidelberg, 2012. (Year: 2012).*

(Continued)

*Primary Examiner* — Carol Wang
(74) *Attorney, Agent, or Firm* — Guy Tucker

(57) ABSTRACT

Video processing for motor task analysis is described. In various examples, a video of a person carrying out a motor task, such as placing the forefinger on the nose, is input to a trained machine learning system to classify the motor task into one of a plurality of classes. In an example, motion descriptors such as optical flow are computed from pairs of frames of the video and the motion descriptors are input to the machine learning system. The motor task analysis may (Continued)

be used to assess or evaluate neurological conditions such as multiple sclerosis and/or Parkinson's.

18 Claims, 12 Drawing Sheets

(51) Int. Cl.
*G16H 50/20* (2018.01)
*G06N 20/00* (2019.01)
*G06F 16/955* (2019.01)
*G06N 5/02* (2006.01)
*G06K 9/62* (2006.01)
*G06N 5/00* (2006.01)
*G06T 7/20* (2017.01)
*G06T 7/00* (2017.01)
*G06F 19/00* (2018.01)
*G16H 20/40* (2018.01)

(52) U.S. Cl.
CPC ....... *G06K 9/00744* (2013.01); *G06K 9/6267* (2013.01); *G06K 9/6278* (2013.01); *G06N 5/00* (2013.01); *G06N 5/025* (2013.01); *G06N 20/00* (2019.01); *G06T 7/0012* (2013.01); *G06T 7/20* (2013.01); *G16H 50/20* (2018.01); *G06F 19/3481* (2013.01); *G06K 2009/00738* (2013.01); *G06T 2207/10016* (2013.01); *G06T 2207/20081* (2013.01); *G16H 20/40* (2018.01)

(58) Field of Classification Search
CPC ................. G06F 19/00; G06F 19/3481; G06F 17/30784; G06F 17/30887; G06F 3/017; G06T 7/0012; G06T 7/20; G06T 2207/10016; G06T 2207/20081; G06T 2207/30016; G16H 50/20; G06N 5/00; G06N 5/025; G06N 99/005; A61B 5/4082; A61B 5/4094; A61B 5/4064; A61B 5/11; A61B 5/112; A61B 5/1124; A61B 2018/00446

See application file for complete search history.

(56) References Cited

U.S. PATENT DOCUMENTS

| | | | |
|---|---|---|---|
| 8,213,678 B2* | 7/2012 | Willmann ............ | A61B 5/0064 382/103 |
| 2002/0087269 A1* | 7/2002 | Sasaki ................... | B60R 1/00 701/301 |
| 2004/0193413 A1* | 9/2004 | Wilson .................. | G06F 3/017 704/243 |
| 2004/0228503 A1 | 11/2004 | Cutler | |
| 2006/0018516 A1* | 1/2006 | Masoud ............ | G06K 9/00342 382/115 |
| 2006/0045185 A1 | 3/2006 | Kiryati et al. | |
| 2006/0098845 A1* | 5/2006 | Sotriropoulos .... | G06K 9/00335 382/107 |
| 2007/0177792 A1* | 8/2007 | Ma ..................... | G06K 9/00348 382/155 |
| 2009/0299232 A1* | 12/2009 | Lanfermann ........ | A61B 5/1122 600/595 |
| 2010/0127981 A1 | 5/2010 | Brandt et al. | |
| 2011/0044501 A1* | 2/2011 | Tu ...................... | G06F 3/017 382/103 |
| 2011/0182469 A1* | 7/2011 | Ji ....................... | G06K 9/00335 382/103 |
| 2011/0263946 A1 | 10/2011 | El Kaliouby | |
| 2012/0214594 A1* | 8/2012 | Kirovski ................ | A63F 13/42 463/36 |
| 2012/0218177 A1* | 8/2012 | Pang .................... | G06F 3/0346 345/156 |
| 2012/0235903 A1* | 9/2012 | Im ......................... | G06F 3/005 345/158 |
| 2013/0156297 A1 | 6/2013 | Shotton et al. | |
| 2013/0294651 A1* | 11/2013 | Zhou .................. | G06K 9/00355 382/103 |
| 2014/0119608 A1 | 5/2014 | Lett et al. | |
| 2014/0142439 A1* | 5/2014 | French ................ | A61B 5/4088 600/483 |
| 2014/0221869 A1* | 8/2014 | Martinez-Conde ........................ | A61B 5/1103 600/558 |
| 2014/0314269 A1* | 10/2014 | Chen .................. | G06K 9/00335 382/103 |
| 2014/0379292 A1* | 12/2014 | Ara .......................... | A61B 5/11 702/141 |
| 2015/0157202 A1 | 6/2015 | Brandt et al. | |
| 2015/0309583 A1* | 10/2015 | Lim ....................... | G06F 3/017 345/156 |
| 2016/0027325 A1* | 1/2016 | Malhotra ............ | G06F 19/3481 434/252 |
| 2016/0071284 A1* | 3/2016 | Kontschieder ........ | G06F 16/783 382/107 |
| 2016/0148391 A1* | 5/2016 | Chua .................. | G06K 9/00342 382/103 |

FOREIGN PATENT DOCUMENTS

| | | |
|---|---|---|
| WO | 2007/029012 A1 | 3/2007 |
| WO | 2014/127065 A2 | 8/2014 |

OTHER PUBLICATIONS

Zhu, Guangyu, Changsheng Xu, Wen Gao, and Qingming Huang. "Action recognition in broadcast tennis video using optical flow and support vector machine." In Computer Vision in Human-Computer Interaction, pp. 89-98. Springer Berlin Heidelberg, 2006. (Year: 2006).*

Ke, Yan, Rahul Sukthankar, and Martial Hebert. "Efficient visual event detection using volumetric features." In Computer Vision, 2005. ICCV 2005. Tenth IEEE International Conference on, vol. 1, pp. 166-173. IEEE, 2005. (Year: 2006).*

Ribeiro, Pedro Canotilho, and José Santos-Victor. "Human activity recognition from video: modeling, feature selection and classification architecture." In Proceedings of International Workshop on Human Activity Recognition and Modelling, pp. 61-78. 2005. (Year: 2005).*

Schwarz, Loren Arthur, Artashes Mkhitaryan, Diana Mateus, and Nassir Navab. "Human skeleton tracking from depth data using geodesic distances and optical flow." Image and Vision Computing 30, No. 3 (2012): 217-226. (Year: 2012).*

Efros, Alexei, Alexander C. Berg, Greg Mori, and Jitendra Malik. "Recognizing action at a distance." In Computer Vision, 2003. Proceedings. Ninth IEEE International Conference on, pp. 726-733. IEEE, 2003. (Year: 2003).*

Nakata, Toru. "Recognizing human activities in video by multi-resolutional optical flows." In Intelligent Robots and Systems, 2006 IEEE/RSJ International Conference on, pp. 1793-1798. IEEE, 2006. (Year: 2006).*

Holte, Michael B., Thomas B. Moeslund, and Preben Fihl. "View-invariant gesture recognition using 3D optical flow and harmonic motion context." Computer Vision and Image Understanding 114, No. 12 (2010): 1353-1361. (Year: 2010).*

Brand, Matthew, and Vera Kettnaker. "Discovery and segmentation of activities in video." IEEE Transactions on Pattern Analysis and Machine Intelligence 22, No. 8 (2000): 844-851. (Year: 2000).*

Hoai, Minh, Zhen-Zhong Lan, and Fernando De la Torre. "Joint segmentation and classification of human actions in video." In Computer Vision and Pattern Recognition (CVPR), 2011 IEEE Conference on, pp. 3265-3272. IEEE, 2011. (Year: 2011).*

Lv, Fengjun, and Ramakant Nevatia. "Recognition and segmentation of 3-d human action using hmm and multi-class adaboost." In European conference on computer vision, pp. 359-372. Springer Berlin Heidelberg, 2006. (Year: 2006).*

(56) References Cited

OTHER PUBLICATIONS

Lin, Ting-Yang, Chung-Hung Hsieh, and Jiann-Der Lee. "A kinect-based system for physical rehabilitation: Utilizing tai chi exercises to improve movement disorders in patients with balance ability." In Modelling Symposium (AMS), 2013 7th Asia, pp. 149-153. IEEE, 2013. (Year: 2013).*
De Morais, Wagner O., and Nicholas Wickström. "A serious computer game to assist Tai Chi training for the elderly." In Serious Games and Applications for Health (SeGAH), 2011 IEEE 1st International Conference on, pp. 1-8. IEEE, 2011. (Year: 2011).*
Roy, Anil K., Yash Soni, and Sonali Dubey. "Enhancing effectiveness of motor rehabilitation using kinect motion sensing technology." In Global Humanitarian Technology Conference: South Asia Satellite (GHTC-SAS), 2013 IEEE, pp. 298-304. IEEE, 2013. (Year: 2013).*
Çeliktutan, Oya, Ceyhun Burak Akgul, Christian Wolf, and Bülent Sankur. "Graph-based analysis of physical exercise actions." In Proceedings of the 1st ACM international workshop on Multimedia indexing and information retrieval for healthcare, pp. 23-32. ACM, 2013. (Year: 2013).*
Pogorelc, Bogdan, Zoran Bosnić, and Matjaž Gams. "Automatic recognition of gait-related health problems in the elderly using machine learning." Multimedia Tools and Applications 58, No. 2 (2012): 333-354. (Year: 2012).*
Karaman, Svebor, et al. "Hierarchical Hidden Markov Model in detecting activities of daily living in wearable videos for studies of dementia." Multimedia tools and applications 69, No. 3 (2014): 743-771. (Year: 2014).*
Tahir, Nooritawati Md, and Hany Hazfiza Manap. "Parkinson Disease Gait Classification based on Machine Learning Approach." J. Appl. Sci. Faisalabad (Faisalabad) 12 (2012): 180-185. (Year: 2012).*
Iarlori, Sabrina, et al. "RGB-D video monitoring system to assess the dementia disease state based on recurrent neural networks with parametric bias action recognition and DAFS index evaluation." In International Conference on Computers for Handicapped Persons, pp. 156-163. Springer, Cham, 2014. (Year: 2.*
Soran, Bilge, Jenq-Neng Hwang, Su-In Lee, and Linda Shapiro. "Tremor detection using motion filtering and SVM." In Proceedings of the 21st International Conference on Pattern Recognition (ICPR2012), pp. 178-181. IEEE, 2012. (Year: 2012).*
S.A. Solla, et al: "Large margin DAGs for multiclass classification", MIT Press, pp. 547-553, (2000).
Atallah et al: "Real-Time Activity Classification Using Ambient and Wearable Sensors", IEEE Transactions on Information Technology in Biomedicine, 2009, vol. 13, No. 6, pp. 1031-1039.
Poppe, "A survey on vision-based human action recognition", Image and Vision Computing, 2010, vol. 28, pp. 976-990.
Wikipedia, "Motion field", Aug. 2, 2011, found online https://en.wikipedia.org/w/index.php?title=motion_field&oldid=442673803.
Wikipedia, "Optical flow", Apr. 19, 2016, found online https://en.wikipedia.org/w/index.php?title=optical_flow&oldid.
Li et al: "Classifying Normal and Abnormal Status Based on Video Recordings of Epileptic Patients", The Scientific World Journal, 2014, vol. 20, pp. 605-606.
Wikipedia, "Motion detection", Dec. 4, 2015, found online https://en.wikipedia.org/w/index.php?title=motion_detection&oldid.

* cited by examiner

MOTOR TASK ANALYSIS SYSTEM AND METHOD

CROSS-REFERENCE TO RELATED APPLICATION

This application claims priority to U.S. Provisional Application Ser. No. 62/048,132 entitled Video Processing For Motor Task Analysis, filed on Sep. 9, 2014, the entire disclosure of which is incorporated herein by reference for all purposes.

STATEMENT OF JOINT RESEARCH AGREEMENT

The invention claimed herein arose from joint research under a joint research agreement between Microsoft Research Limited and Novartis Pharma AG.

BACKGROUND

Performance of motor tasks such as lifting an arm, standing upright, raising a leg and others typically vary considerably between individuals. For example, depending on body structure, body weight, and other factors such as the expertise and skill of the individual, experience, strength, and physical ability. Existing methods of analysis of motor task performance typically involve manual observation and as such are subjective and open to variation depending on the skill of the observer in making the analysis.

The embodiments described below include, but are not limited to, implementations which solve described disadvantages of known motor task analysis systems.

SUMMARY

Embodiments of the invention comprise a system, apparatus and method for capturing and analyzing movement and/or motor coordination information and/or corresponding activity levels, from a patient, also sometime referred to herein as a person, and/or a subject. Embodiments of the invention further comprise a system, apparatus and method for capturing and analyzing movement and motor movement and/or coordination information including corresponding patient or subject activity levels. Embodiments of the invention further comprise a system, apparatus and method for capturing and analyzing movement and motor movement and/or coordination information including corresponding patient or subject activity levels contextualized by or with biomarkers, sensors and/or patient or stand-alone devices which act to facilitate at least one of data capture, storage, exchange or analysis.

Embodiments of the system comprise an automated intelligent computer system that captures and scores one or more physical aspects including but not limited to patient or subject motion, neurological coordination, gait and motor coordination, movement, flexion of limbs, position of limbs, reaction to stimuli, body posture, and physical appearance, e.g. major components of a neurological evaluation.

An embodiment of the system is used as a scoring or evaluation tool for a subject or patient.

Embodiments of the invention provide for sensitive and observer-independent assessment of motor-related neurological function.

Embodiments of the invention provide for automated, touch-free reliable assessment of motor dysfunction and/or normal function.

In some embodiments, video processing is used motor task analysis. In various examples, a video of at least part of a person or animal carrying out a motor task, such as placing the forefinger on the nose, is input to a trained machine learning system to classify the motor task into one of a plurality of classes. In an example, motion descriptors such as optical flow are computed from pairs of frames of the video and the motion descriptors are input to the machine learning system. For example, during training the machine learning system identifies time-dependent and/or location-dependent acceleration or velocity features which discriminate between the classes of the motor task. In examples, the trained machine learning system computes, from the motion descriptors, the location dependent acceleration or velocity features which it has learned as being good discriminators. In various examples, a feature is computed using a single sub-volume of the video, or by comparing two sub-volumes of the video.

Embodiments of the invention provide an apparatus, system and method to assess, evaluate and/or diagnose a disease or condition by imaging a motion whereby the effects of the disease or condition on a patient's motion and/or physical activity are captured. There are a number of diseases or conditions which are known to exhibit neurological effects, or which affect or impact a patient's motion, or some aspect of movement. Such diseases or conditions comprise, for example Parkinson's Disease, Huntington's disease, Amyotrophic Lateral Sclerosis (ALS) commonly referred to as "Lou Gehrig's Disease," and cerebral palsy are well known examples. Other diseases and conditions are known which may impair motion and/or activity, such as Rheumatoid Arthritis, muscle wasting or chronic obstructive pulmonary disease (COPD). Still other diseases and conditions may exhibit some effect on motion and activity, for example Autism, schizophrenia, and Alzheimer's disease. By way of further example, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders such as tremors, Parkinson's disease, multiple sclerosis and spasticity, which may result in irregular movement or activity, other neurological disorders, or a generally decreased level of activity. The difficulty walking or otherwise moving experienced by patients with movement disorders may cause such patients to avoid movement to the extent possible. Further, depression or other neuropsychiatric disorders such as dementia, depression, mania, bipolar disorder, and obsessive-compulsive disorder, or conditions such as congestive heart failure, cardiac arrhythmia, gastrointestinal disorders, and incontinence are other examples of disorders that may generally cause a patient to be less active. When a patient is inactive, the patient may be more likely to be recumbent, i.e., lying down, sitting, etc., and may change postures less frequently.

Embodiments of the invention permit the selection and/or administration of appropriate therapeutic drugs or other therapeutic forms indicated for motor diseases and/or neurological conditions by assessment of one or more of patient neurologic behavior, gait, and motor coordination and activity levels. In addition, these metrics are important measures of long-term functional recovery. Embodiments of the invention permit an automated, accurate and repeatable evaluation of motor function on a test group of patients and/or subjects in the course of clinical trials to determine the safety and efficacy of a new medical treatment, for example, a new drug.

Embodiments of the invention provide a system, apparatus and method by which motor activity and/or dysfunction can be accurately determined and changes in motor functions reliably detected. Embodiments of the invention provide for such a system, apparatus and method which can be used by the patient at the patient's home or office, and without the need for special or dedicated sensors or computer equipment, and which is readily usable by young and old patients alike. An embodiment of the invention comprises a computer-implemented method comprising: providing a machine learning system; training the machine learning system to find location-dependent local motion features of videos which discriminate between a plurality of classes of a motor task; receiving a video depicting at least part of a person or animal performing a motor task; inputting the video to the trained machine learning system; receiving, from the trained machine learning system, data about which of the plurality of classes the motor task is predicted to belong to; and evaluating a neurological disease or condition of the person or animal performing the motor task.

Embodiments of the invention comprise a method comprising: receiving video data comprising a plurality of frames, at least two frames comprising a digital representation of a human performing a motor task; mapping a plurality of reference points for each of the at least two frames of the video data to the digital representation of the human in the at least two frames of the video data; calculating a plurality of motion descriptors for the at least two frames of the video data, each motion descriptor corresponding to one of the reference points; and assessing one or more of a disease status and a disease severity based on at least one of the motion descriptors. In some embodiments, this method further is further characterized by a disease severity sub-score which is indicative of one or more symptoms selected from ataxia; truncal ataxia; gait ataxia; limb ataxia; spasticity; tremor; weakness; dysmetria; upper extremity motor dysfunction; dexterity; mobility; leg function, and combinations thereof.

An embodiment of the system is used to evaluate or assess a patient who has been diagnosed with or is suspected of having a neurological condition, for example multiple sclerosis or Parkinson's.

Embodiments of the invention provide for such a system, apparatus and method which can be used by the patient remotely, such as a system deployed on a smartphone, or other personal/portable/mobile computing device.

Many of the attendant features will be more readily appreciated as the same becomes better understood by reference to the following detailed description considered in connection with the accompanying drawings. It is to be noted that, as used herein, a "motor task" is a selected or defined movement of some element of human or animal anatomy, involving a motor or muscular component.

DESCRIPTION OF THE DRAWINGS

The present description will be better understood from the following detailed description read in light of the accompanying drawings, wherein.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples. Note that the terms "patient", "subject" and "person" are used interchangeably unless otherwise clear from the context.

Figure 1:
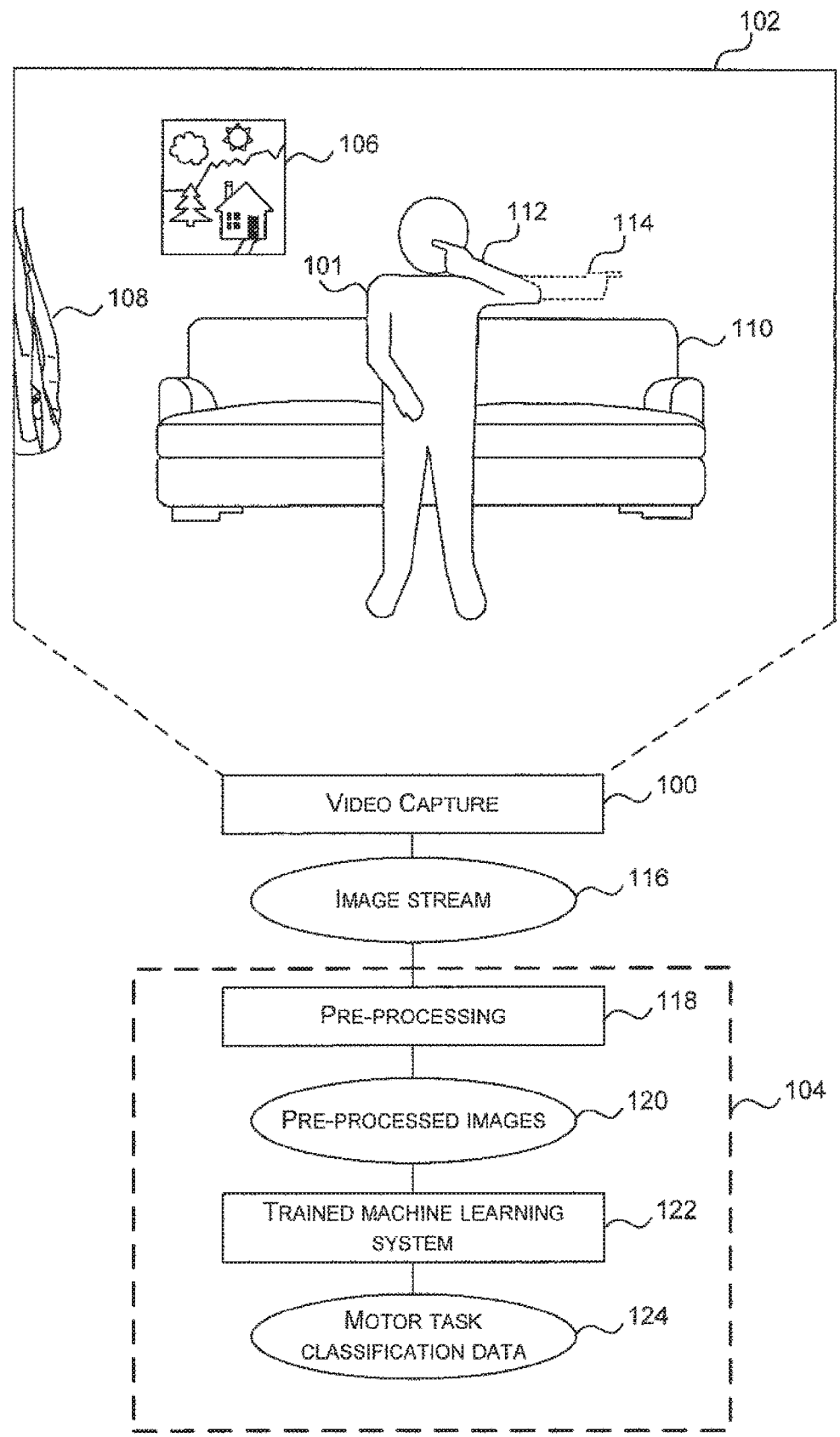
FIG. 1 is a schematic diagram of video capture of a person carrying out a motor task, and showing processing of the video to analyze the motor task.

FIG. 1 is a schematic diagram of a person 101 performing a motor task such as placing a forefinger on the nose (as indicated by arm position 112) after starting from a position where the arm is outstretched horizontally (as indicated by arm position 114). This is only one example of a motor task and more are given below with reference to FIGS. 2 and 12.

Analyzing motor tasks has previously been achieved manually (e.g. by visual observation) which is subject to variability such as biases of the observer, observer experience level, and the observer environment. In various examples described below, videos of motor tasks are processed to analyze the motor tasks. For example, to classify the motor tasks into two or more classes such as good, medium, weak (for example, to indicate performance level of the motor task). By using an automated, video processing system as described herein it is possible to obtain unbiased, accurate ratings/classifications in a fast and practical manner.

In some examples, the proposed system exhibits the following advantages: An assessment can be performed by a clinician, technician, nurse or by patients themselves. The assessment is consistent by design, since every assessment is performed by the same algorithm. The system can assess the condition more sensitively, since it is not limited by human perception. Finally, the system can be used by patients at home, or even remotely, allowing frequent assessment without the need to travel to a medical center or schedule a visit.

A video capture device 100 captures video of a person 101 carrying out a motor task in an environment, which in the example of FIG. 1 is a room with a picture 106 on the wall, a couch 110, and a garment 108 hanging on the wall. However, this is an example only and other environments may be used. The video capture device 100 may be mounted on the wall facing the user or may be supported in another manner such as on a computing device, table or other structure. The video capture device 100 is described in more detail with reference to FIG. 2. It captures an image stream 116 comprising a plurality of frames captured at a frame rate such as 30 frames per second or more. Other frame rates can be used depending on the type of motor task and video capture equipment. Videos of people are captured with appropriate consent and the video material is preferably stored in a secure, private manner.

The captured frames may be input to a computing device 104 which may be integral with the video capture device 100 or may be connected to the video capture device using wireless communications, wired connection or in other ways. The computing device 104 may be in the cloud, provided as a cloud service. The example of FIG. 1 shows a single computing device 104. However, it is also possible to use a plurality of distributed computing devices which together provide the functionality.

The computing device 104 of FIG. 1 comprises a pre-processing component 118 which pre-processes the video to produce pre-processed images 120. Thus, in some embodiments, pre-processing is used to standardize the videos, so that e.g. similar locations in space have similar meanings, and/or to remove information that has little to do with the actual motor function or dysfunction being assessed. The computing device 104 also comprises a trained machine learning system 122 such as a random decision forest, an ensemble of support vector machines, or other trained machine learning system which outputs motor task classification data 124.

The machine learning system is trained to learn location-dependent, local motion features which are good discriminators of the motor task classes. For example, randomly selected local motion features can be assessed during training and those which perform good discrimination are selected. Location-dependent features are characteristics of one or more sub-volumes of the video. The sequence of frames forming a video can be thought of as forming a volume and a sub-volume in a contiguous region of the larger volume. Characteristics of a sub-volume are location dependent because the sub-volume is at a particular location in time and space of the video. Local motion features are characteristics of one or more sub-volumes related to how image elements within frames of the sub-volume change location between the image frames. For example, the local motion features may relate to velocity or acceleration of image elements. The term acceleration is used here to refer to rate of change of either magnitude of velocity, or rate of change of direction of velocity, or both rate of change of magnitude and direction of velocity. It has been found that location-dependent local motion features can provide effective discriminators for motor task classes as explained in more detail in this document.

Figure 2:
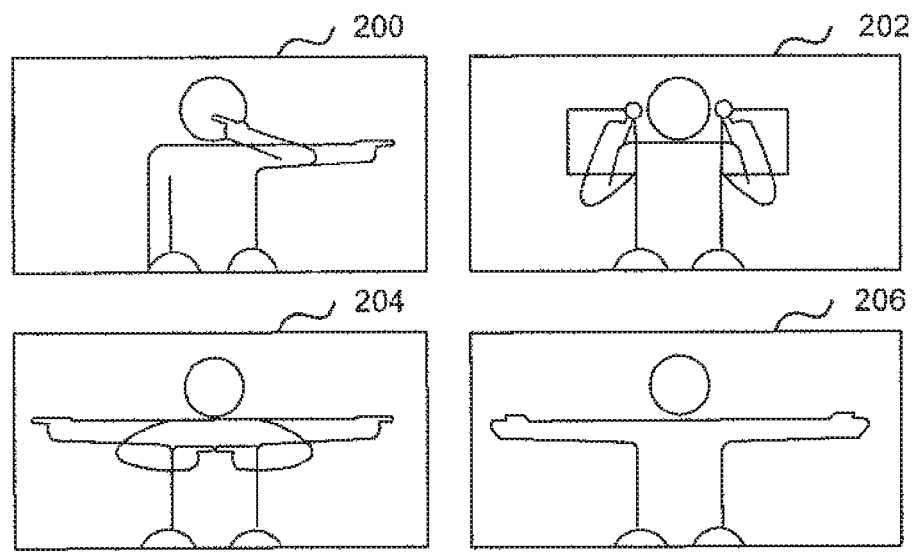
FIG. 2 is a schematic diagram of examples of motor tasks.

FIG. 2 is a schematic diagram of exemplary types of motor tasks which may be analyzed. A first motor task is a finger to nose task 200, which involves a person raising an arm to a horizontal position extending away from the body and pointing the forefinger; the person then moves the arm by bending the elbow so as to place the forefinger on the nose without allowing the arm to vary from the horizontal position. Typically, the test is performed with each arm, and repeated three times each. This test may be performed with the subject's eyes open, with eyes closed, or both (i.e., at least once each).

A finger to finger task 204 involves raising both arms to shoulder height horizontal positions extending away from the body with the forefingers pointing away from the body. The person then moves both arms so that the forefingers me at et in front of the body and touches the forefingers together with the arms remaining horizontal. This motion is repeated three times. This test may be performed with the subject's eyes open, with eyes closed, or both (i.e., at least once each).

In another motor task, referred to as a drawing squares task 202, a person draws two imaginary-equal sized squares in the air in front of the body at eye level, one with each forefinger. The squares extend from eye level down to the chest, out toward the sides of the body, back up to eye level, and then back in toward the body. The squares are drawn simultaneously with both hands. This test may be performed with the subject's eyes open, with eyes closed, or both (i.e., at least once each).

A truncal ataxia task 206 involves a person starting in the seated position and extending both arms out horizontally to the sides of and away from the body with the palms down. Simultaneously, the person extends both legs in front of and away from the body, holds the position for at least five seconds, and then returns to the starting position. This test may be performed with the subject's eyes open, with eyes closed, or both (i.e., at least once each).

More examples of motor tasks are described with reference to FIG. 12.

A drinking from a cup motor task 1200, comprises an act in which a seated person grasps a cup in one hand, picks it up, and sips from it, then replaces the cup and repeats the motion using the other hand.

A normal walking motor task 1202 involves a person walking in a normally toward the image/video capture device until reaching the image/video capture device.

A hopping on one foot task 1204 involves a person standing, raising one foot of the ground (and possibly balancing by placing hands on a stationary object or another person), and hopping with vigor on the other foot closest to the image/video capture device ten times.

A Romberg task 1206 involves holding both arms at the sides of the body, raising the arms and hands up to shoulder height in a horizontal position in front of the body, palms up. This position is held for five seconds, then eyes are closed, and the position is held for five more seconds before returning the arms to the sides of the body.

A turning on the spot task 1208 involves a person standing with arms at sides of the body and turning 360° without taking any side steps, as best as possible.

In a turning pages task 1210, a person turns three pages of a book using the left hand in a reading direction (right to left) and then turns three pages in the opposite direction using the right hand.

A straight-line walking task 1212 involves the person walking along a straight line toward the image/video capture device, one foot in front of the other heel to toe, until reaching the image/video capture device.

Figure 12:
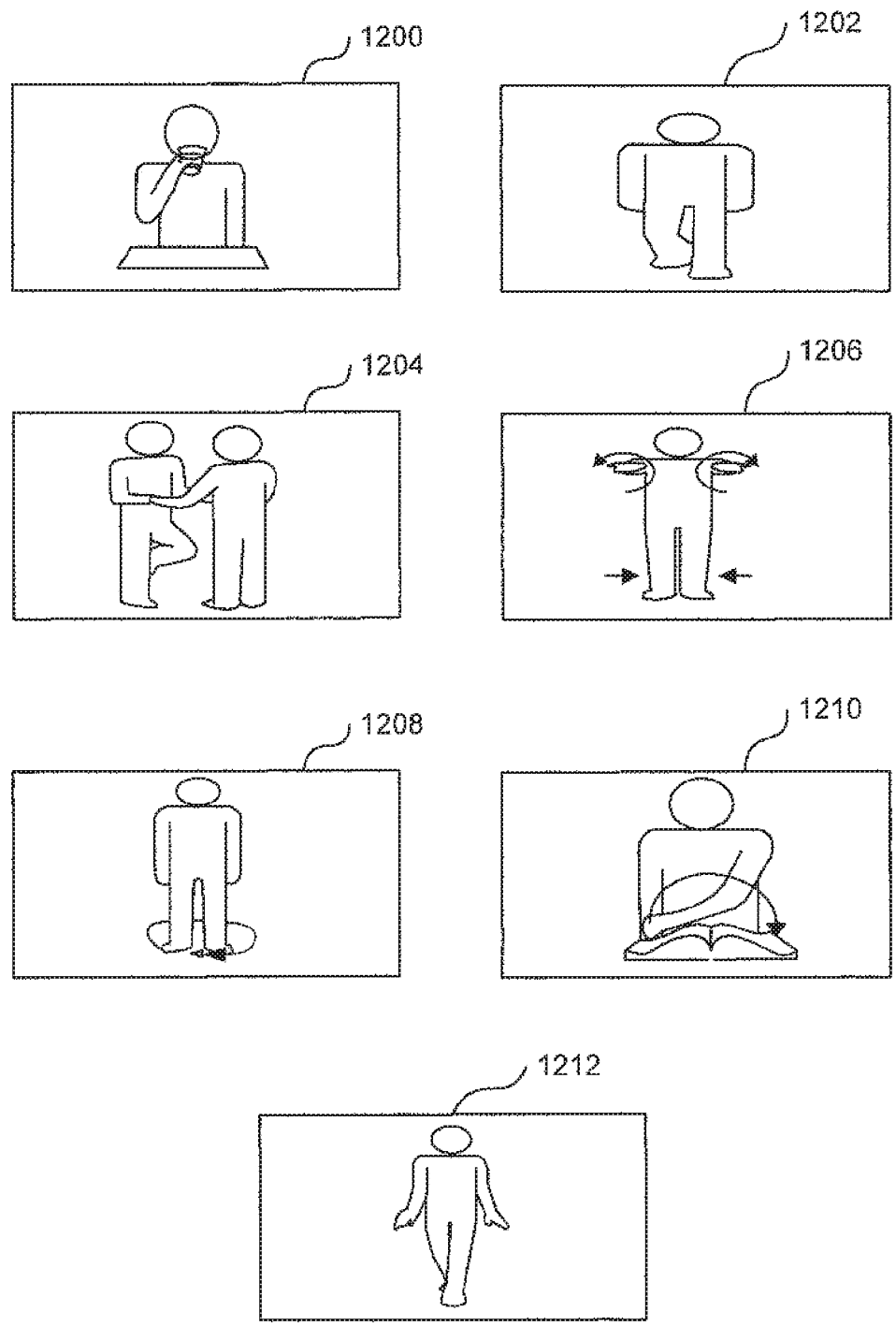
FIG. 12 is a schematic diagram of additional examples of motor tasks Like reference numerals are used to designate like parts in the accompanying drawings.

The examples of motor tasks provided in FIG. 2 and FIG. 12 are not an exhaustive list of examples of possible motor tasks, but are provided to illustrate the technology. Moreover, the number of repetitions and task durations are exemplary only, and may be modified as evident to one skilled in the art.

In some embodiments, specific motor tasks are selected to both provide reliable imaging results and to correlate well with neurological conditions for evaluation. Some motor tasks which are suitable for these purposes are shown in FIGS. 2 and 12, which may be used alone or along with other motion tasks to aid in making automated assessments.

Figure 3:
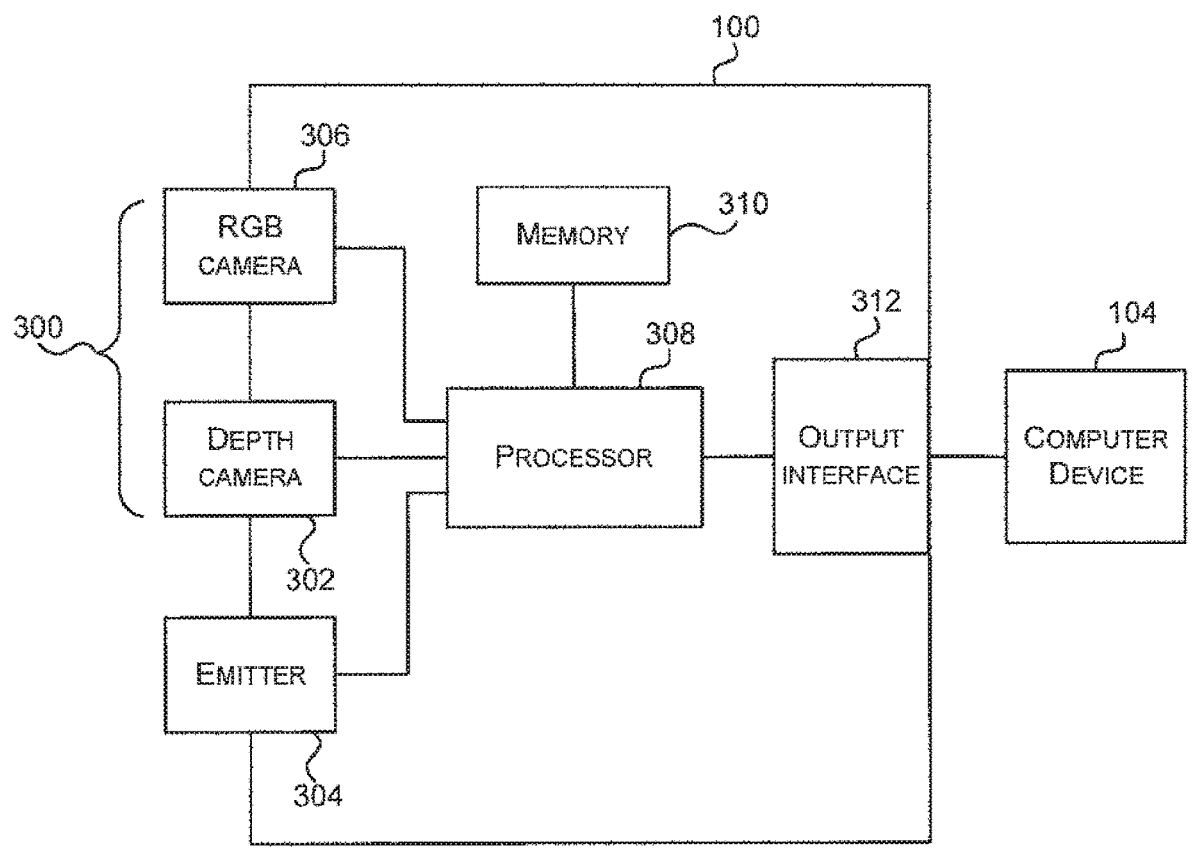
FIG. 3 is a schematic diagram of a capture device which may be used in the scenario of FIG. 1.

Reference is now made to FIG. 3, which illustrates a schematic diagram of an example video capture device 100 that can be used in the camera-based system of FIG. 1. In the example of FIG. 3 the video capture device 100 is configured to capture depth videos (using depth camera 302) as well as color videos (using RGB camera 306). Embodiments of the invention may be configures to capture only color videos, or only depth videos. Where a depth camera 302 is used it can be of any suitable type, for example, time-of-flight, structured light, stereo, or suitable combinations. The depth camera may use speckle decorrelation in some examples. Where a color video camera is used, facial features or other visual features which may identify a person may be redacted from the color video. In some embodiments, color video may be used together with depth video, and images concatenated.

The video capture device 100 comprises at least one imaging sensor 300. In the example shown in FIG. 3, the imaging sensor 300 comprises a depth camera 302 arranged to capture a depth image of a scene. The captured depth image can include a two-dimensional (2-D) area of the captured scene where each image element in the 2-D area represents a depth value such as a length or distance of an object in the captured scene from the depth camera 302.

The capture device can also include an emitter 304 arranged to illuminate the scene in such a manner that depth information can be ascertained by the depth camera 302. For example, in embodiments where the depth camera 302 is an infra-red (IR) time-of-flight camera, the emitter 304 emits infrared (IR) light onto the scene, and the depth camera 302 is arranged to detect backscattered light from the surface of one or more targets and objects in the scene. In some examples, pulsed infrared light can be emitted from the emitter 304 such that the time between an outgoing light pulse and a corresponding incoming light pulse can be detected by the depth camera and measured and used to determine a physical distance from the video capture device 100 to a position on the targets or objects in the scene. Additionally, in some examples, the phase of the outgoing light wave from the emitter 304 can be compared to the phase of the incoming light wave at the depth camera 302 to determine a phase shift. The phase shift can then be used to determine a physical distance from the capture device 100 to a position on the targets or objects. In a further example, time-of-flight analysis can be used to indirectly determine a physical distance from the capture device 100 to a position on the targets or objects by analyzing the intensity of the reflected beam of light over time via various techniques including, for example, shuttered light pulse imaging.

In other embodiments, the capture device 100 can use structured light to capture depth information. In such a technique, patterned light (e.g., light displayed as a known pattern such as grid pattern or a stripe pattern) can be projected onto the scene using the emitter 304. Upon striking the surface of one or more targets or objects in the scene, the pattern becomes deformed. Such a deformation of the pattern can be captured by the depth camera 302 and then be analyzed to determine a physical distance from the capture device 100 to a position on the targets or objects in the scene.

In some embodiments, the depth camera 302 can be in the form of two or more physically separated cameras that view a scene from different angles, such that visual stereo data is obtained that can be resolved to generate depth information. In this case the emitter 304 can be used to illuminate the scene or can be omitted.

In some embodiments, in addition to or instead of the depth camera 302, the capture device 100 can comprise an RGB camera 306. The RGB camera 306 is arranged to capture sequences of images of the scene at visible light frequencies, and can hence provide images that can be used to augment and/or replace the depth images. In some examples depth may be computed from the RGB images without the need for a depth camera 306.

For example, the RGB images may be captured without the use of a depth camera, and depth may be computed from the RGB images, for example by image reconstruction techniques, to provide data that may be used in a similar fashion to the depth images.

The capture device 306 shown in FIG. 3 further comprises at least one processor 308, which is in communication with the imaging sensor 300 (i.e., depth camera 302 and RGB camera 306 in the example of FIG. 3) and the emitter 304. The processor 308 can be a general purpose microprocessor, or a specialized signal/image processor. The processor 308 is arranged to execute instructions to control the imaging sensor 300 and emitter 304 to capture depth videos and/or RGB videos. In some embodiments f the invention, the processor 308 can optionally be arranged to perform processing on these videos.

The capture device 306 shown in FIG. 3 may further include a memory 310 arranged to store instructions for execution by the processor 308, videos or frames of videos captured by the depth camera 302 or RGB camera 306, or any other suitable information, images, or the like. In some embodiments, the memory 310 can include random access memory (RAM), read only memory (ROM), cache, Flash memory, a hard disk, or any other suitable storage component. The memory 310 can be a separate component in communication with the processor 308 or integrated into the processor 308.

The capture device 100 also comprises an output interface 312 in communication with the processor 308 and is arranged to provide data to the computing device 104 via a communication link. The communication link can be, for example, a wired connection (such as USB, Firewire, Ethernet or similar) and/or a wireless connection (such as WiFi, Bluetooth or similar). In other examples, the output interface 312 can interface with one or more communication networks (such as the internet) and provide data to the computing device 104 via these networks.

Figure 4:
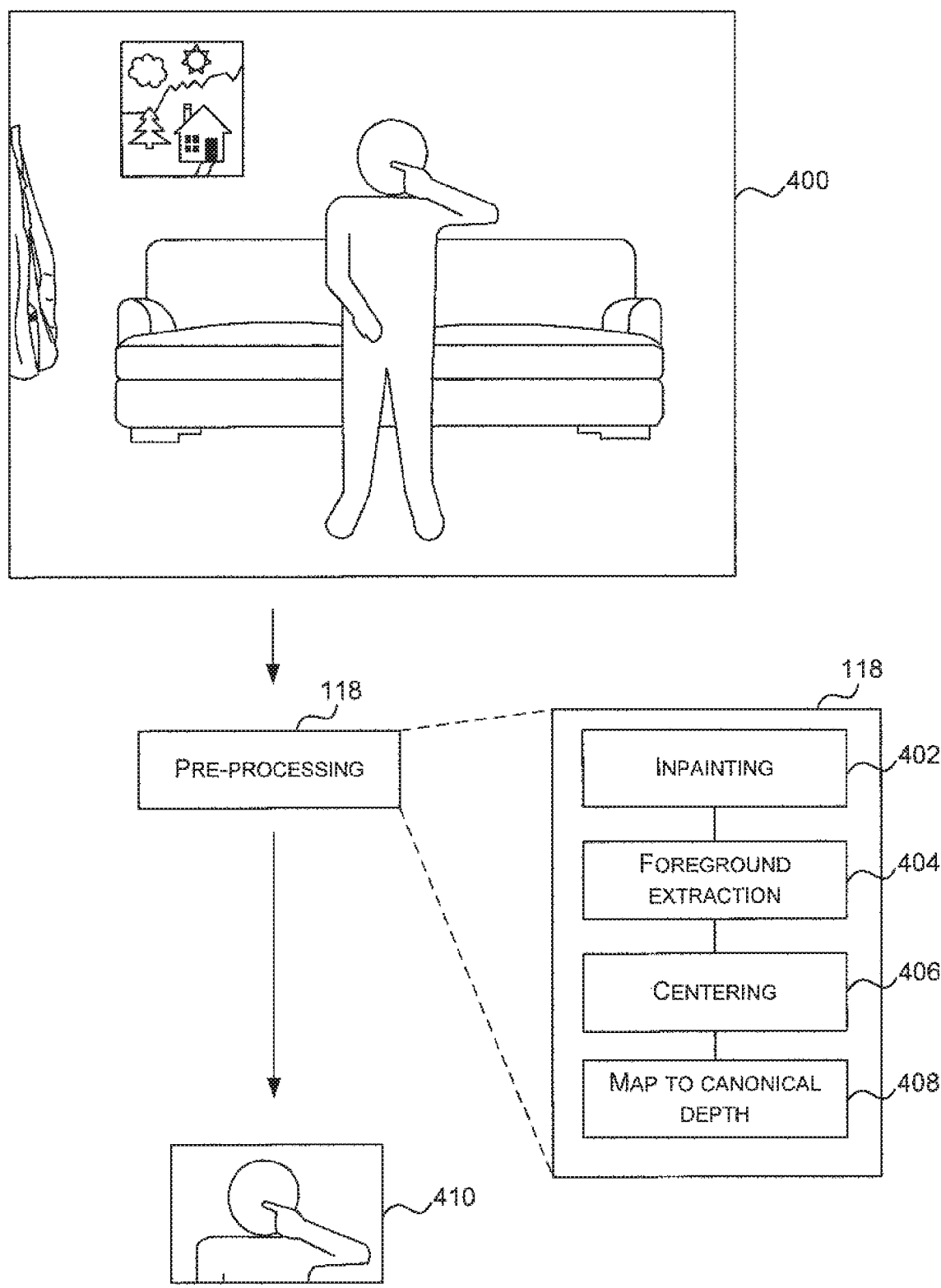
FIG. 4 is a schematic diagram of a frame of the video of FIG. 1 and the result of pre-processing the frame, as well as a pre-processing apparatus.

FIG. 4 is a schematic diagram of a frame 400 of the video of FIG. 1 and the result 410 of pre-processing the frame, as well as a pre-processing apparatus 118. The frame of the video 400 depicts the person slightly off center in this example and at an arbitrary depth from the capture device. The preprocessing apparatus 118 optionally carries out inpainting 402, carries out foreground extraction 404, centering 406 and, in the case depth information is available, maps the foreground to a canonical depth. In this way comparisons between frames of the pre-processed video can be made more simply than if pre-processing did not occur. Inpainting 402 may be used where the foreground comprises image elements with missing or erroneous values, for example due to noise. This is particularly useful where a depth video camera is used. Inpainting may comprise filling in missing image element values with values calculated on the basis of nearest neighbors of the missing image element, or in other well-known ways.

Foreground extraction 404 may be carried out using depth data (in the case depth data is available), for example, using a Gaussian model of depths followed by a geodesic refinement stage. A Gaussian model of depths may comprise a Gaussian mixture model fitted to a histogram of depths observed in a frame. In an example, the first Gaussian mode is taken as corresponding to the foreground. However, other modes or combinations of modes may be used. A geodesic refinement stage may comprise using the image elements that have depth values falling in the most frequent depth range as a seed region and computing geodesic distances of each other image element from the seed region. The geodesic distances may then be used to refine the foreground region using thresholding.

In embodiments using color videos, foreground extraction 404 may be achieved by using color data, by identifying edges in the image, or in other ways.

The centering process 406 may comprise using template-matching to detect a head or other specified body part of the person depicted in the frame. Once detected this body part may be centered in the pre-processed image 410 and scaled or mapped 408 to a canonical depth (in the case that depth frames are involved). In other examples the centering process comprises computing a center of mass of the foreground region and aligning the center of mass with a center of the pre-processed image. In the case that a color video is used the body part is scaled to a specified size rather than mapping to a canonical depth.

In embodiments of the invention which comprise a machine learning system, it may be trained to find location-dependent local motion features which are good discriminators of the motor task classes. The machine learning system may be trained using labeled videos 500 of motor tasks (see FIG. 5). The labels indicate which class the depicted motor task falls into. The labels may be assigned by human judges for example. The labeled videos may be of different lengths. The labeled videos are pre-processed using preprocessing apparatus 118 described above to produce training data 502. Motion descriptors are computed 504 from the training data videos and the motion descriptors are used by a trainer 506 to produce a trained machine learning system 508. For example, the trained machine learning system comprises a random decision forest, an ensemble of randomized support vector machines, neural networks, or boosting systems.

Embodiments of the process of computing the motion descriptors 504 may comprise selecting pairs of video frames 510 from one of the videos (from training data 502) and computing motion descriptors indicating magnitude and/or direction of motion (or change in these quantities) of image elements between the pairs of video frames, otherwise known as a "pairwise" analysis. A pair of frames may be two consecutive frames. For example, motion descriptors may be computed for each pair of consecutive frames in a training video and input to the trainer. In some embodiments, the motion descriptors 504 comprise optical flow values. Optical flow values are vertical and horizontal displacement values of an image element depicting the same scene element in a pair of video frames. Using optical flow values as the motion descriptors has been found to give robust, accurate results. In embodiments of the invention, accuracy is at least 80%, or 85% or 90% or more. In another example the motion descriptors 504 comprise displacements of body joint positions between pairs of video frames. In another example the motion descriptors 504 comprise displacements of body part centroids between pairs of video frames. In another example the motion descriptors comprise the area of non-overlap between the foreground region of one frame and the foreground region of another frame.

Figure 5:
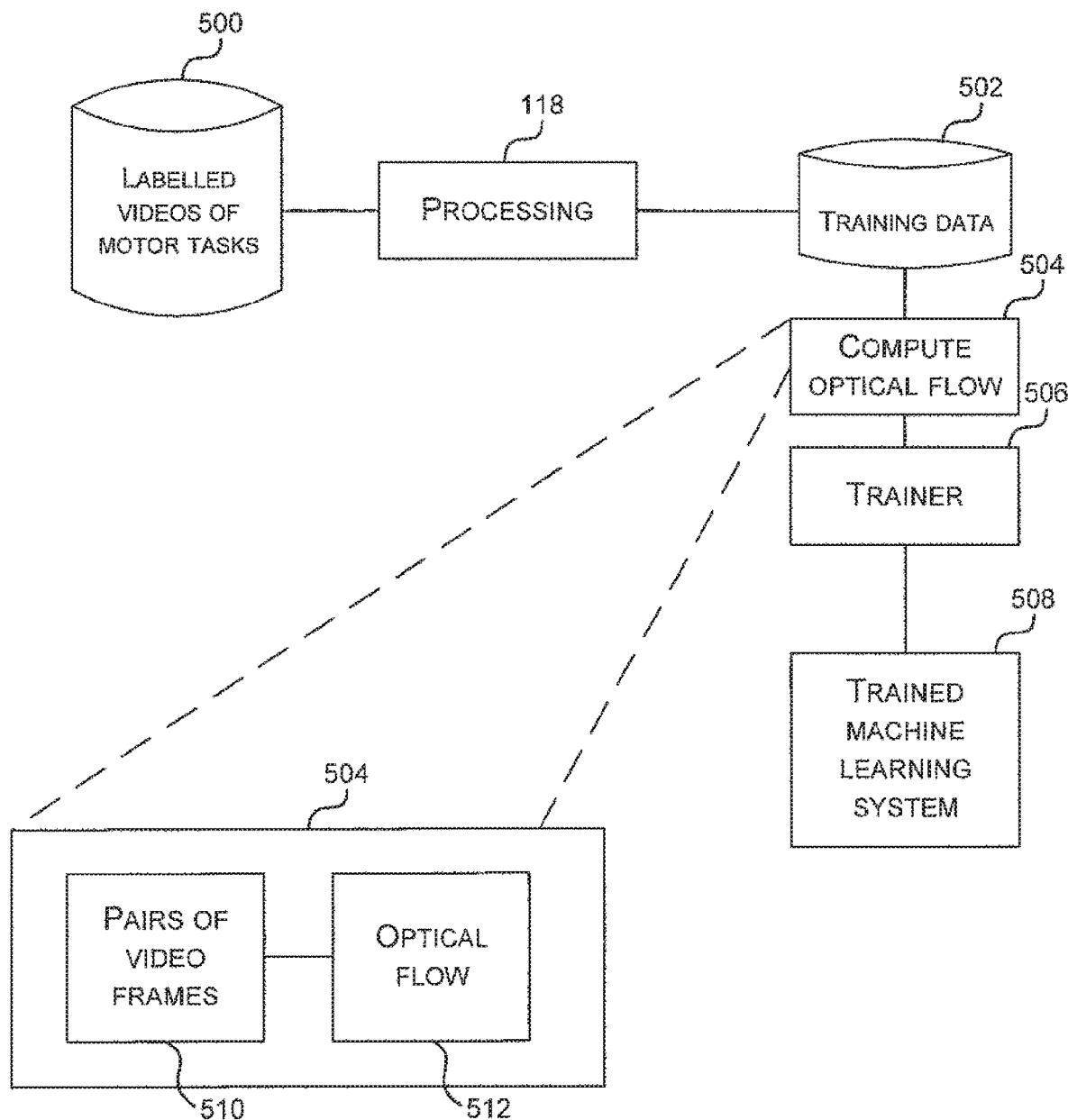
FIG. 5 is a schematic diagram of a system for training a machine learning system to analyze videos of motor tasks.

In the example of FIG. 5 the motion descriptors are computed in advance of input to the trainer. This may also be done at test time. Where the video is long and the image size is large, the number of motion descriptors to be computed is potentially very large, (for all pairs of consecutive frames for example) and so it may be beneficial to pre-compute the motion descriptors. However, it is also possible to compute the motion descriptors as part of the training and/or test phases. The test phase is when the trained machine learning system is used on previously unseen videos (that is, videos not yet presented to the machine learning system).

In some embodiments, the machine learning system comprises a random decision forest. A random decision forest comprises one or more decision trees each having a root node, a plurality of split nodes and a plurality of leaf nodes. A video is pushed through trees of a random decision forest from the root to a leaf node in a process whereby a decision is made at each split node. The decision is made according to location-dependent local motion features as described in more detail below. At a split node the video proceeds to the next level of the tree down a branch chosen according to the results of the decision. The random decision forest may use regression or classification as described in more detail below. During training, parameter values (which specify the location-dependent local motion features) are learnt for use at the split nodes and data (labeled videos) is accumulated at the leaf nodes. The labels of the videos accumulated at a leaf node may be stored as a histogram, or in an aggregated manner, such as using a mean, median or mode or by fitting a probability distribution to the histogram and storing statistics describing the probability distribution.

At system test a previously unseen video is input to the system to have one or more motor task classes predicted. This is described with reference to FIG. 8.

Figure 6:
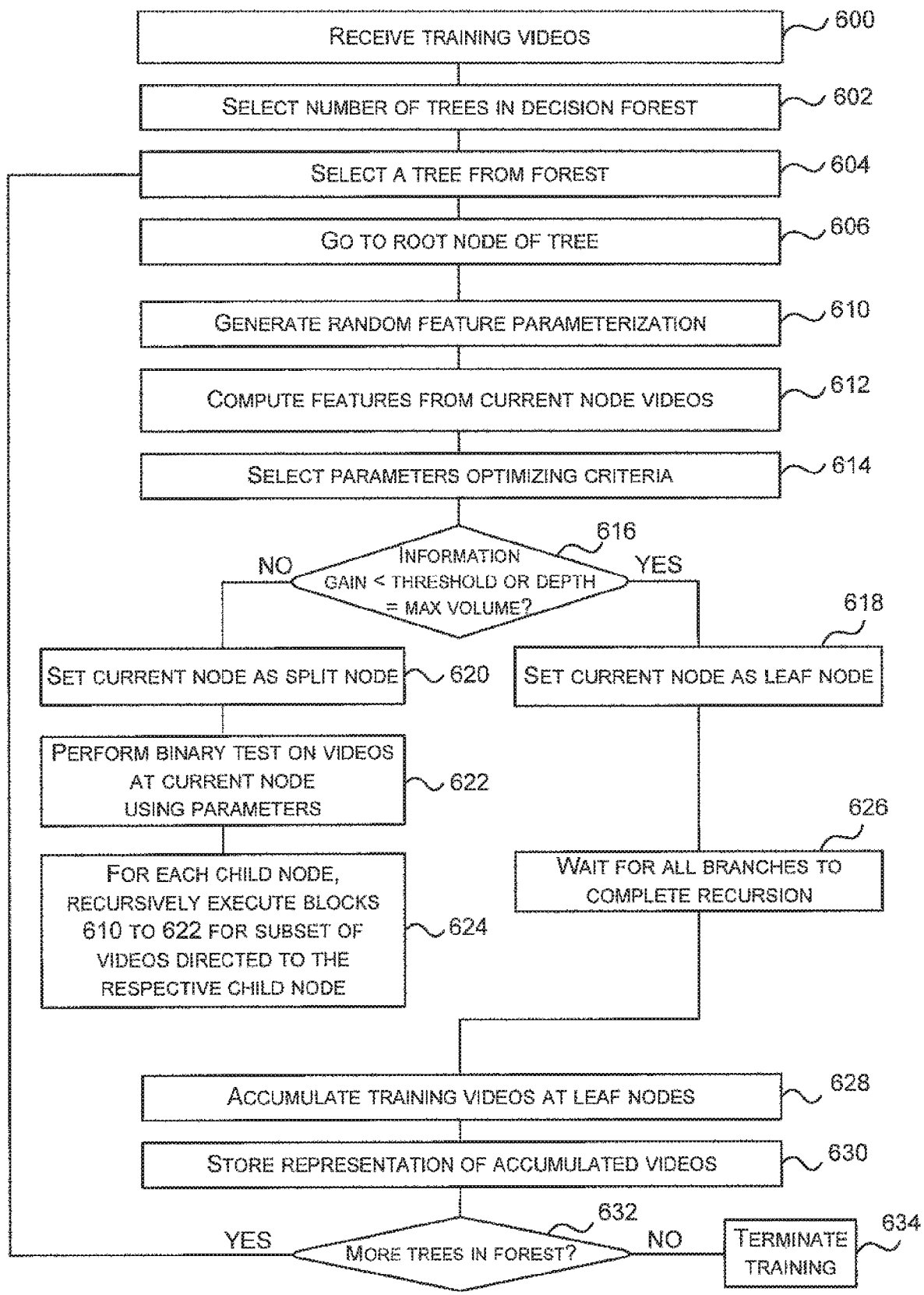
FIG. 6 is a flow diagram of a method of training a random decision forest to classify videos of motor tasks.

Referring to FIG. 6, to train the decision trees, the training set described above is first received 600. The number of decision trees to be used in a random decision forest is selected 602. A random decision forest is a collection of deterministic decision trees. Decision trees can be used in classification or regression algorithms, but can suffer from over-fitting, i.e. poor generalization. However, an ensemble of many randomly trained decision trees (a random forest) yields improved generalization. During the training process, the number of trees is fixed.

Figure 7:
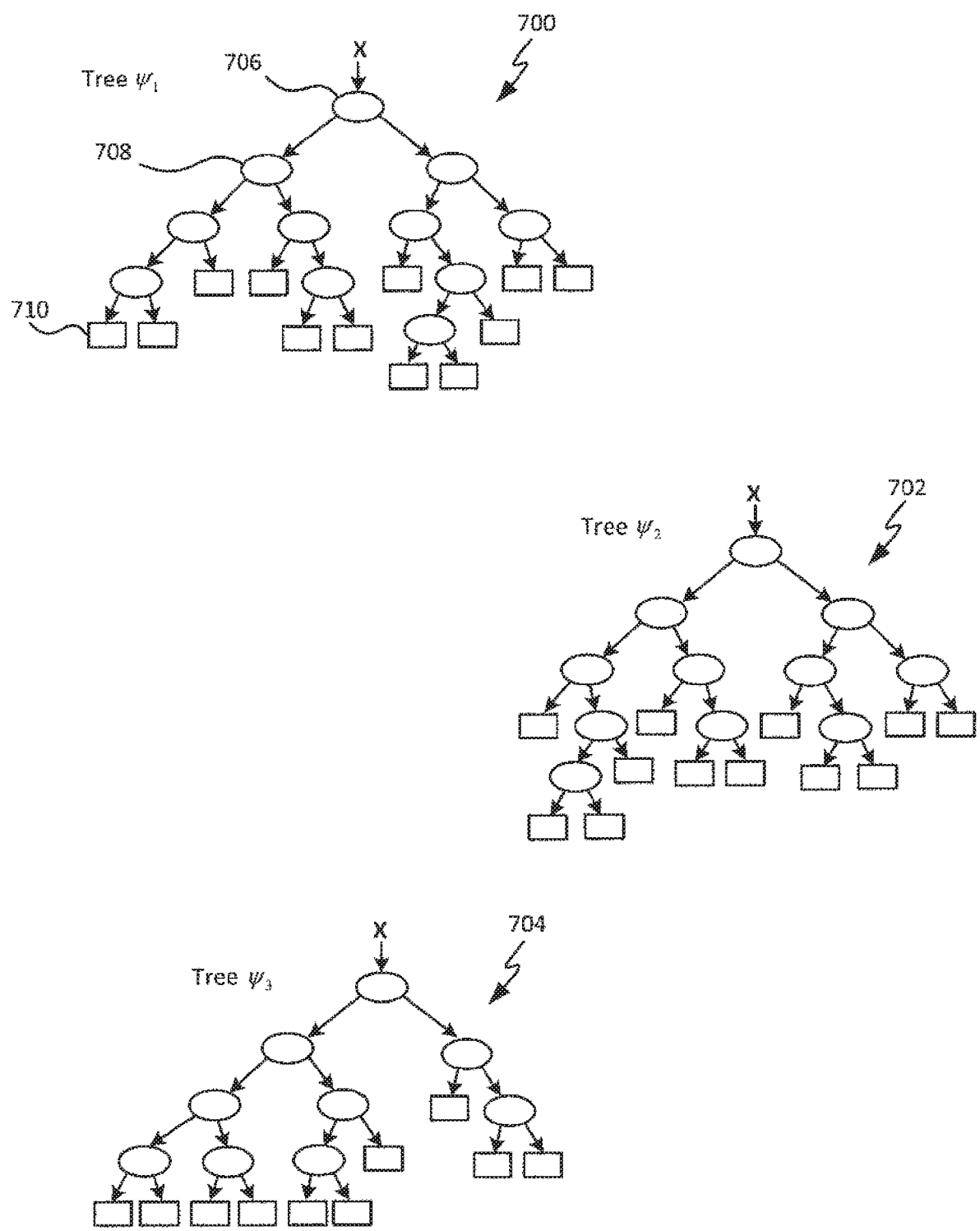
FIG. 7 is a schematic diagram of a random decision forest.

An example random decision forest is shown illustrated in FIG. 7. The illustrative decision forest of FIG. 7 comprises three decision trees: a first tree 700; a second tree 702; and a third tree 704. Each decision tree comprises a root node (e.g. root node 706 of the first decision tree 700), a plurality of internal nodes, called split nodes (e.g. split node 708 of the first decision tree 700), and a plurality of leaf nodes (e.g. leaf node 710 of the first decision tree 700).

A decision tree from the decision forest is selected 604 (e.g. the first decision tree 600) and the root node 606 is selected 606. A random set of test parameters are then generated 610 for use by a binary test performed at the root node as candidate features. In the examples described herein location-dependent local motion features are used. The locations within the video, in 2D within a frame, and/or in time within the sequence of frames, are selected at random. The features are randomly generated from a plurality of different types of features. For example, the following four types of feature are used which relate to sub-volumes of the video. A sub-volume of the video may be a cuboid selecting a space-time window in the video. A sub-volume may be denoted by symbol B and may be specified by 2D horizontal and vertical image coordinates within a first frame, and 2D horizontal and vertical image coordinates within a second frame, where the number of frames between the first and second frames is specified. For example, $B=(x_1,x_2,y_1,y_2,T'_1,T'_2)$. However, it is not essential to use cuboid shaped sub-volumes. Other 3D shapes of sub-volume may also be used.

A first type of feature is a function of a single sub-volume. An example of a first type of feature is denoted by $f(d_1,B_1)$ which may be expressed in words as a function of a parameter $d_1$ which indicates the type of local motion feature to compute within sub-volume $B_1$. More details about example functions f which may be used are given below.

A second type of feature is a function of two sub-volumes. An example of a second type of feature is denoted by $f(d_1,B_1)+f(d_2,B_2)$ which may be expressed in words as the sum of: a function of a parameter $d_1$ which indicates the type of local motion feature to compute within sub-volume $B_1$, and a function of a parameter $d_1$ which indicates the type of local motion feature to compute within sub-volume $B_1$.

A third type of feature is a function of two sub-volumes. An example of a third type of feature is denoted by $f(d_1,B_1)-f(d_2,B_2)$ which may be expressed in words as the difference of: a function of a parameter $d_1$ which indicates the type of local motion feature to compute within sub-volume $B_1$, and a function of a parameter $d_1$ which indicates the type of local motion feature to compute within sub-volume $B_1$.

A fourth type of feature is a function of two sub-volumes. An example of a fourth type of feature is denoted by $|f(d_1,B_1)-f(d_2,B_2)|$ which may be expressed in words as the absolute difference of: a function of a parameter $d_1$ which indicates the type of local motion feature to compute within sub-volume $B_1$, and a function of a parameter $d_1$ which indicates the type of local motion feature to compute within sub-volume $B_1$.

The function f may be computed by aggregating local motion features such as acceleration or velocity features. An example in which acceleration features are computed is now given.

$$f(d, B) = \frac{1}{(y_2 - y_1)(x_2 - x_1)} \sum_{x'=x_1}^{x_2} \sum_{y'=y_1}^{y_2} \tilde{A}_d^{T(B)}(x', y')$$

Where T(B) is the number of frames of a sub-volume and the symbol A is an estimated acceleration feature (an example of a local motion feature) which may be computed as explained below for each image element location in the sub-volume (or a sub-set of these locations). The above function may be expressed in words as a function f of a given local motion feature type and a given sub-volume is computed as an average of the acceleration features per frame of the subvolume.

The estimated acceleration feature A may be calculated by counting the number of times the rate of change of optical flow vectors changes direction, but ignoring changes of direction where the magnitude of the optical flow vectors is very small (by using a Heaviside step function or a threshold or in other ways).

In another example an estimated velocity feature may be used in place of the estimated acceleration feature above. For example, by counting the number of times the optical flow vectors change direction rather than considering the rate of change of the optical flow vectors.

At step 610 of FIG. 6 a random set of test parameters is generated 610 for use by a binary test performed at a split node as candidate features. In an example, these parameters may include parameters of the sub-volume(s) (i.e. specifying the locations and duration of the sub-volumes to be used), a threshold parameter (for comparing the features against in the binary test), the parameter d which indicates the type of local motion feature to compute (e.g. velocity in the x direction, velocity in the y direction, acceleration in the x direction, acceleration in the y direction), and a variable k selecting one of the four (or other number of) features above.

Then, every combination of test parameter may be applied 612 to each video which has reached the current node. For each combination, criteria (also referred to as objectives) are calculated 614. In an example, the calculated criteria comprise the information gain (also known as the relative entropy). The combination of parameters that optimize the criteria (such as maximizing the information gain is selected 614 and stored at the current node for future use. As an alternative to information gain, other criteria can be used, such as Gini entropy, or the 'two-ing' criterion or others.

It is then determined 616 whether the value for the calculated criteria is less than (or greater than) a threshold. If the value for the calculated criteria is less than the threshold, then this indicates that further expansion of the tree does not provide significant benefit. This gives rise to asymmetrical trees which naturally stop growing when no further nodes are beneficial. In such cases, the current node is set 618 as a leaf node. Similarly, the current depth of the tree is determined (i.e. how many levels of nodes are between the root node and the current node). If this is greater than a predefined maximum value, then the current node is set 618 as a leaf node. Each leaf node has labeled videos which accumulate at that leaf node during the training process as described below.

It is also possible to use another stopping criterion as an alternative or in combination with those already mentioned, for example, an assessment of the number of videos that reach the node. If there are too few examples (compared with a threshold for example) then the process may be arranged to stop to avoid overfitting. However, it is not essential to use this stopping criterion.

If the value for the calculated criteria is greater than or equal to the threshold, and the tree depth is less than the maximum value, then the current node is set 620 as a split node. As the current node is a split node, it has child nodes, and the process then moves to training these child nodes. Each child node is trained using a subset of the training videos at the current node. The subset of videos sent to a child node is determined using the parameters that optimized the criteria. These parameters are used in the binary test, and the binary test performed 622 on all videos at the current node. The videos that pass the binary test form a first subset sent to a first child node, and the image elements that fail the binary test form a second subset sent to a second child node.

For each of the child nodes, the process as outlined in blocks 610 to 622 of FIG. 6 are recursively executed 624 for the subset of videos directed to the respective child node. In other words, for each child node, new random test parameters are generated 610, applied 612 to the respective subset of videos, parameters optimizing the criteria selected 614, and the type of node (split or leaf) determined 616. If it is a leaf node, then the current branch of recursion ceases. If it is a split node, binary tests are performed 622 to determine further subsets of videos and another branch of recursion starts. Therefore, this process recursively moves through the tree, training each node until leaf nodes are reached at each branch. As leaf nodes are reached, the process waits 626 until the nodes in all branches have been trained. Note that, in other examples, the same functionality can be attained using alternative techniques to recursion.

Once all the nodes in the tree have been trained to determine the parameters for the binary test optimizing the criteria at each split node, and leaf nodes have been selected to terminate each branch, then video labels may be accumulated 628 at the leaf nodes of the tree. A representation of the accumulated video labels may be stored 630 using various different methods.

Once the accumulated video labels have been stored it is determined 632 whether more trees are present in the decision forest. If so, then the next tree in the decision forest is selected, and the process repeats. If all the trees in the forest have been trained, and no others remain, then the training process is complete and the process terminates 634.

Therefore, as a result of the training process, one or more decision trees are trained using empirical training videos. Each tree comprises a plurality of split nodes storing optimized test parameters, and leaf nodes storing associated labeled videos or representations of aggregated video labels. Due to the random generation of parameters from a limited subset used at each node, the trees of the forest are distinct (i.e. different) from each other.

The training process may be performed in advance of using the trained prediction system to identify motor task classes in a video. The decision forest and the optimized test parameters may be stored on a storage device for use in identifying motor task classes at a later time.

Figure 8:
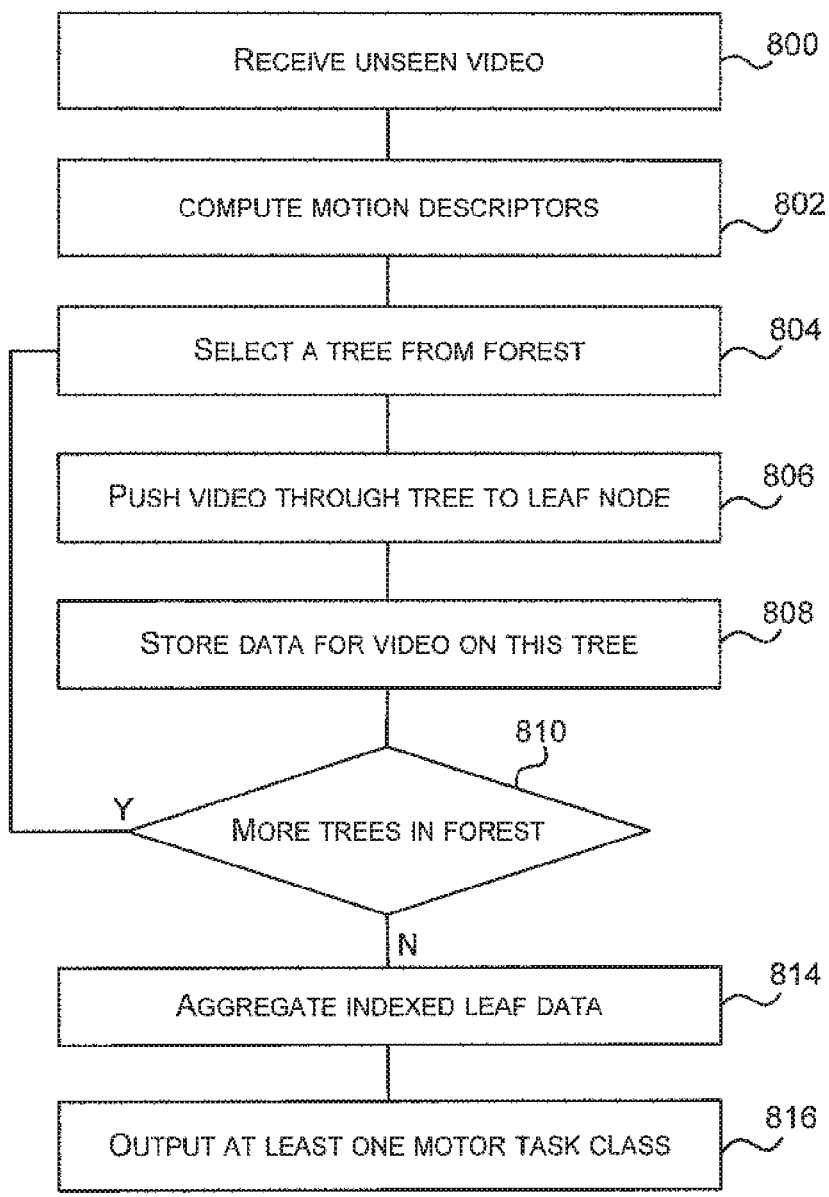
FIG. 8 is a flow diagram of a method of using a trained random decision forest to classify a motor task video.

FIG. 8 illustrates a flowchart of a process for predicting motor task classes in a previously unseen video using a decision forest that has been trained as described above. First, an unseen video is received 800. A video is referred to as 'unseen' to distinguish it from a training video which has the motor task class specified. Note that the unseen video can be pre-processed to an extent, as described above, with reference to FIG. 4.

Optical flow or other motion descriptors are computed 802. A trained decision tree from the decision forest is also selected 804. The selected video is pushed 806 through the selected decision tree (in a manner similar to that described above with reference to FIGS. 6 and 7), such that it is tested against the trained parameters at a node, and then passed to the appropriate child in dependence on the outcome of the test, and the process repeated until the video reaches a leaf node. Once the video reaches a leaf node, the accumulated labels associated with this leaf node are stored 808 for this video.

If it is determined 810 that there are more decision trees in the forest, then a new decision tree is selected 804, the video pushed 806 through the tree and the accumulated labels stored 808. This is repeated until it has been performed for all the decision trees in the forest. Note that the process for pushing a video through the plurality of trees in the decision forest can also be performed in parallel, instead of in sequence as shown in FIG. 8.

The data from the indexed leaf nodes is aggregated 814 by averaging or in other ways. For example, where histograms of class labels are stored at the leaf nodes the histograms from the indexed leaf nodes are combined and used to identify one or more motor tasks associated with the video. The processes outputs 816 at least one motor task class as a result, and is able to output a confidence weighting of the motor task class. This helps any subsequent algorithm assess whether the proposal is good or not. More than one motor class may be output; for example, where there is uncertainty.

In some embodiments the machine learning system comprises an ensemble of support vector machines. A support vector machine is a non-probabilistic, binary classifier which uses hyperplanes in a feature space to achieve the classification.

In an example, a support vector machine is associated with (or replaces) a split node of a random decision forest such as that described above with reference to FIGS. 6 to 8. The support vector machine takes as input the training videos which have reached the respective split node. These input training videos form its feature space and it calculates one or more hyperplanes to make a binary classification of the feature space. In this way support vector machines are used to make the binary decisions rather than assessing information gain or other criteria as described above for random decision trees. In this way the process of FIG. 6 for training a random decision forest can be adapted to train an ensemble of support vector machines by using a support vector machine at each split node. It is also possible to use mixtures of types of split node (random decision split nodes or support vector machine split nodes). The resulting ensemble of support vector machines or mixture of support vector machines/random decision nodes, may be used at test time by modifying the process of FIG. 8. In this way it is possible to use support vector machine technology for a task involving an extremely high and variable number of dimensions in a practical manner. Training is achieved in a practical time scale because each support vector machine receives only the training videos which reach it through the binary tree structure.

Another example in which an ensemble of randomized support vector machines is used is now given. To train the ensemble of randomized support vector machines, a fixed-length feature vector is calculated from each labeled training video. The fixed-length feature vector comprises a plurality of location-dependent local motion features of the video. For example, any combination of one or more of the four features described above in the description about the random decision forest may be used (although other features may be used). By creating a fixed size feature descriptor, such as a vector or list, the resulting system is operable independently of video length. This is achieved without loss of movement characteristics in the videos; in contrast to temporal normalization techniques.

The features in each feature descriptor are selected at random. The feature descriptors define a feature space where the support vector machines perform learning. In an example, an individual support vector machine of the ensemble is trained to find a hyperplane that maximizes the margin between samples of training videos labeled in the different classes. Each of the support vector machines is trained in this way. The resulting ensemble of randomized support vector machines may be used at test time by modifying the process of FIG. 8.

In the embodiments and examples described above the machine learning system classifies videos of motor tasks into classes or ratings. However, alternatively or additionally, in embodiments of the invention the machine learning system may use regression rather than classification so that continuous valued outputs are obtained from the trained machine learning system, as opposed to discrete class labels. For example, these continuous valued outputs may be numerical values on a motor task assessment scale.

Figure 9:
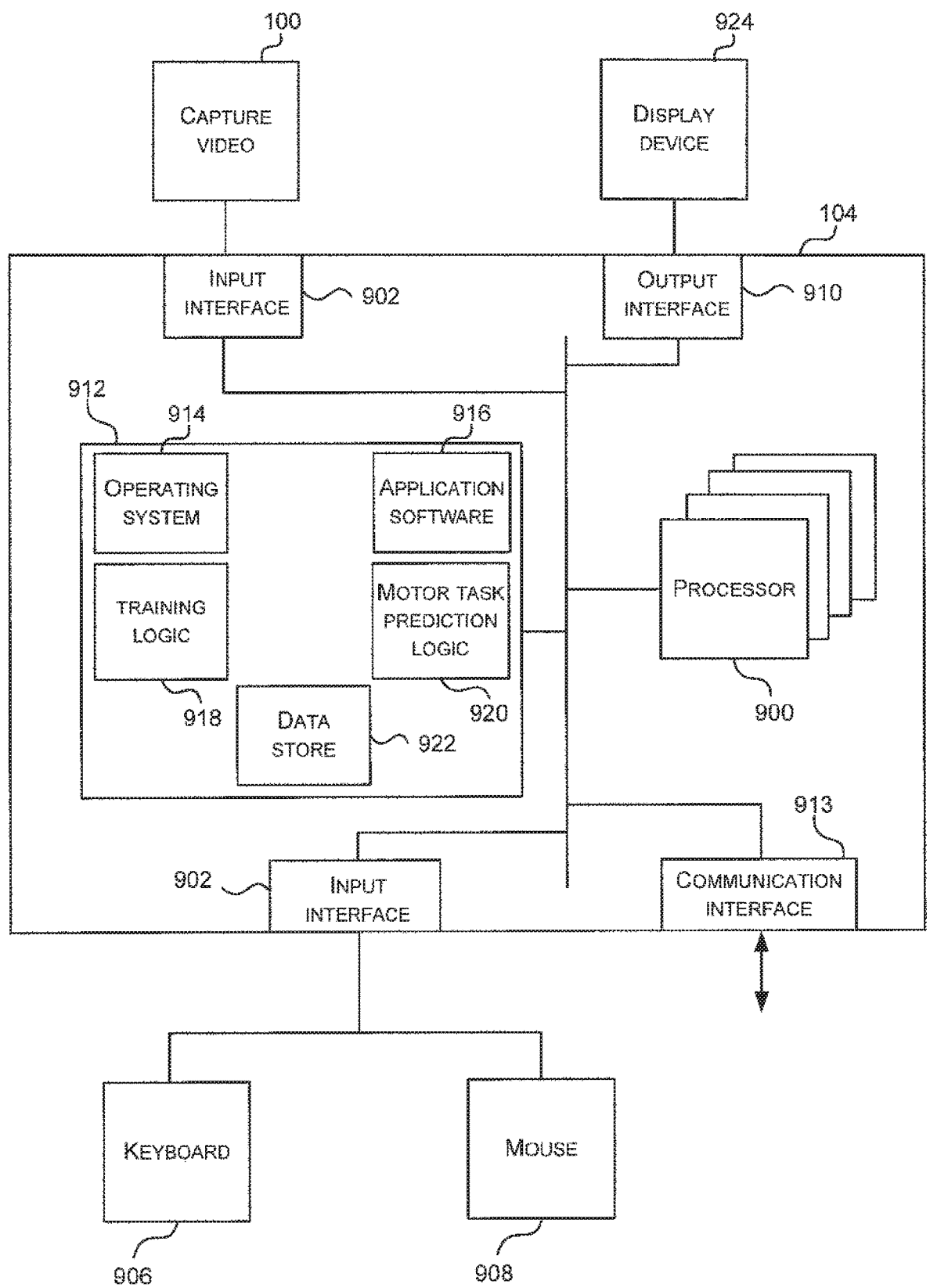
FIG. 9 illustrates an exemplary computing-based device in which embodiments of a video processing system may be implemented.

FIG. 9 illustrates various components of an exemplary computing-based device 104 which may be implemented as any form of a computing and/or electronic device, and in which embodiments of motor task classification systems may be implemented.

Computing-based device 104 comprises one or more processors 900 which may be microprocessors, controllers, graphics processing units, parallel processing units, or any other suitable type of processors for processing computing executable instructions to control the operation of the device in order to predict motor task classes in videos. In some examples, such as team where a system on a chip architecture is used, the processors 900 may include one or more fixed function blocks (also referred to as accelerators) which implement a part of the method of motor task classification in hardware (rather than software or firmware).

The computing-based device 104 comprises one or more input interfaces 902 arranged to receive and process input from one or more devices, such as user input devices (e.g. capture device 100, a keyboard 906 and/or a mouse 908). This user input may be used to control software applications executed on the computing device 104.

The computing-based device 104 also comprises an output interface 910 arranged to output display information to a display device 924 which can be separate from or integral to the computing device 104. For example, to display the videos with superimposed motor task classification data. The display information may provide a graphical user interface. In an example, the display device 924 may also act as the user input device if it is a touch sensitive display device. The output interface may also output data to devices other than the display device, e.g. a locally connected printing device.

The computer executable instructions may be provided using any computer-readable media that is accessible by computing based device 104. Computer-readable media may include, for example, computer storage media such as memory and communications media. Computer storage media, such as memory 912, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer storage media does not include communication media. Therefore, a computer storage medium should not be interpreted to be a propagating signal per se. Propagated signals may be present in a computer storage media, but propagated signals per se are not examples of computer storage media. Although one example of computer storage media (memory 912) is shown within the computing-based device 104 it will be appreciated that the storage may be distributed or located remotely and accessed via a network or other communication link (e.g. using communication interface 913).

Platform software comprising an operating system 914 or any other suitable platform software may be provided at the computing device 104 to enable application software 916 to be executed on the device. Other software that can be executed on the computing device 104 includes: training logic 918 (see for example, FIGS. 6-7 and description above); prediction logic 920 (see for example FIG. 8 and description above). A data store 922 is provided to store data such as previously received videos; intermediate function results; tree training parameters, probability distributions, classification labels, regression objectives, classification objectives, and other data.

Any of the input interface 902, output interface 910, display device 924 and the user input devices 906, 908 may comprise NUI (natural user interface) technology which enables a user to interact with the computing-based device in a natural manner, free from artificial constraints imposed by input devices such as mice, keyboards, remote controls and the like. Examples of NUI technology that may be provided include but are not limited to those relying on voice and/or speech recognition, touch and/or stylus recognition (touch sensitive displays), gesture recognition both on screen and adjacent to the screen, air gestures, head and eye tracking, voice and speech, vision, touch, gestures, and machine intelligence. Other examples of NUI technology that may be used include intention and goal understanding systems, motion gesture detection systems using depth cameras (such as stereoscopic camera systems, infrared camera systems, RGB camera systems and combinations of these), motion gesture detection using accelerometers/gyroscopes, facial recognition, 3D displays, head, eye and gaze tracking, immersive augmented reality and virtual reality systems and technologies for sensing brain activity using electric field sensing electrodes (EEG and related methods).

Figure 10:
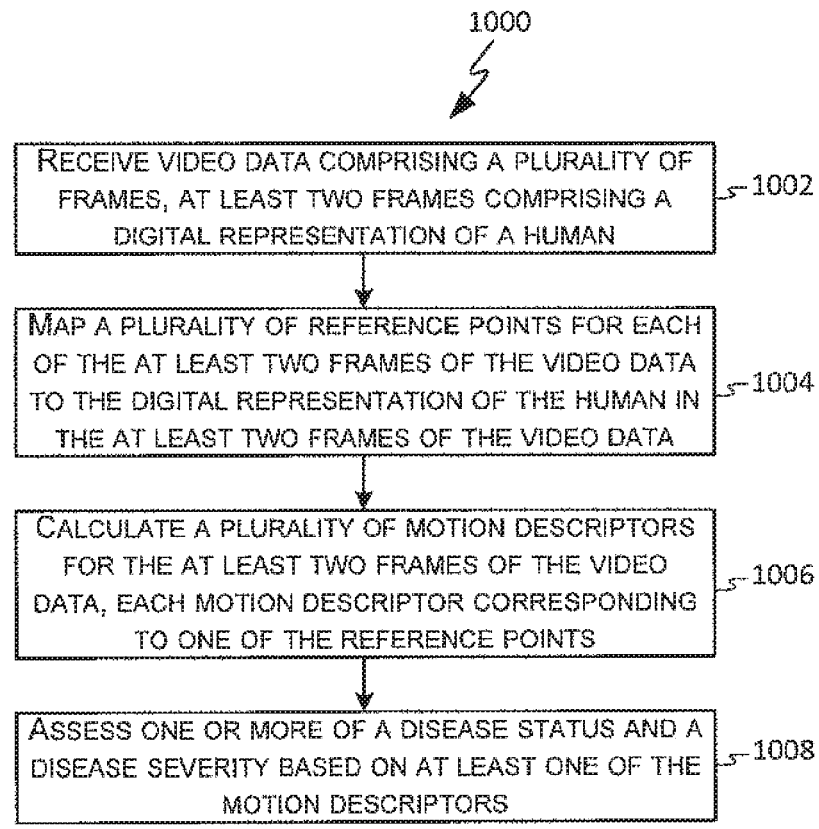
FIG. 10 shows a flowchart of a method according to one embodiment.

Referring now to FIG. 10, a method 1000 for assessing or evaluating a disease, state or condition, or the absence of a disease, state or condition, is shown according to one embodiment. The method 1000 may be performed in accordance with the present invention in any of the environments depicted in FIGS. 1-9, among others, in various embodiments. Of course, more or less operations than those specifically described in FIG. 10 may be included in method 1000, as would be understood by one of skill in the art upon reading the present descriptions. As used herein "disease" or "condition" is meant to refer to a state which can impact, or does impact, any external manifestation of physiological a physiological function such as movement, motor coordination, activity, neurologic behavior or state, and the like. Unless otherwise clear from the context, "disease" and "condition" are used interchangeably.

Each of the steps of the method 1000 may be performed by any suitable component of the operating environment. For example, in one embodiment, the method 1000 may be partially or entirely performed by a controller, a processor, a personal computer system, a laptop computer, a XBOX Kinect system, etc.

In operation 1002, video data is received, such as from a video/image capture device, that includes a plurality of frames. At least two frames comprise a digital representation of a human. The digital representation of the human may be captured using any of the video/image capture devices described herein or others not specifically described herein but known in the art, that is, located where the human is located to record movements of the human. The digital representation of the human may include a video, a series of pictures or frames, depth data, or any other type of digital representation known in the art.

In operation 1004, a plurality of reference points for each of the at least two frames of the video data are mapped to the digital representation of the human in the at least two frames of the video data. This mapping may be performed using any of the various analytical methods described herein, or others not specifically described herein.

In one embodiment, the mapping may include optical flow analysis, where frame-to-frame displacement of each pixel's neighborhood is utilized to provide insight toward movements of the human. Optical flow allows for movement to be characterized without requiring explicit identification of body parts.

In operation 1006, a plurality of motion descriptors are calculated for the at least two frames of the video data. Each motion descriptor corresponds to one of the reference points such that there is a point of reference from which to base each motion descriptor.

In operation 1008, one or more of a disease or condition status and a disease or condition severity are assessed based on at least one of the motion descriptors. A disease or condition status, as used herein, may refer to a type of disease, existence of a disease in the human, non-existence of the disease in the human, a condition, progression, stage, etc., of the disease, or any other status indicator known in the art related to a disease or disease type.

Disease status may include a simple binary assessment of whether the human has a disease or not, or may be more comprehensive and describe nuances of the disease, progression of the disease, etc.

Therefore, disease status may be a qualitative determination of whether or not the human meets a predetermined condition, i.e. a diagnostic, assessment, evaluation or disease or stage.

Disease severity is a quantitative measurement of a particular condition known to be suffered by those afflicted with the disease.

However, there is nothing mutually exclusive about these two concepts. A disease severity score may be quantified and then it may be qualitatively determined whether the human satisfies a particular criterion/condition based on the quantitative score in order to more fully assess the disease and the quality of movement/mobility in the human.

The mapping may provide a movement signature, and from the movement signature, an "acceleration feature" may be calculated that counts the number of reversals of movement directionality within a local neighborhood of each pixel. The location (2D+t) and size of the neighborhood may be learned by an algorithm as described in more detail herein. In a signature extraction step, the key movement characteristics are extracted from the videos to reduce the video data to a set of numbers that are manageable for the computer in the subsequent mapping step. In some embodiments, the relevant information conveyed by the videos comprises movement patterns. Signature extraction can maximize the information content of the movement signatures by deriving a signature for each type of movement. In some embodiments, the movement's signature contains only complementary (orthogonal) aspects, to afford maximum coverage of movement detail.

In one embodiment, the video data may include optical flow information of a type known in the art, such as frame-to-frame displacement of each pixel's neighborhood.

In accordance with the embodiments described herein, at least two frames of the video data are shifted temporally from one another. In a further embodiment, at least a portion of the digital representation of the human may be spatially shifted among the at least two frames of the video data. By spatially and temporally shifted, what is meant is that movement of the person in the video data is captured over time. This allows for movement of the person in the video to be recognized and analysed, so that a plurality of motion descriptors may be calculated across at least two frames of the video data.

According to another embodiment, the video data may include non-contact active three-dimensional (3D) scan information, such as depth of field, depth information from a depth scanner, etc.

In other embodiments, the video data may include a series of still frames produced from a 2D video camera. In a further embodiment, each of the frames of the video data may be a 16-bit grayscale image, with each pixel being characterized by a brightness value in a range represented by 0-65,536. According to another embodiment, the frames of the video data may be a 16-bit, 32-bit, 64-bit, 128-bit, etc., color image, with each pixel being characterized by a brightness value in a range represented by 0-65,536, or some other range indicative of brightness known in the art.

The method 1000 may also include calculating a disease severity score based on at least one of the motion descriptors. The disease severity may be assessed based at least in part on the disease severity score. In one embodiment, the disease severity score may have a value in a range from about 0.0 to about 12.0, indicative of a neurostatus score, a disability status scale, and/or an expanded disability status scale. In some embodiments, a disease severity score may be scaled to have any desired range of values, such as between 0 and 100, 0 and 10, 1 and 10, etc.

The disease severity score may be based at least in part on one or more of a plurality of disease severity sub-scores. Each of the disease severity sub-scores corresponds to a motor task. It should be noted that the use of the term "task" is not limited to a human movement specified herein, but may be virtually any movement of which a subject (human or animal) is capable and which may be defined and repeated.

Any of the motor tasks described herein may be chosen, along with others not specifically described herein. For example, the motor task may be selected from any of: a truncal ataxia task, a finger-to-nose task, a finger-to-finger task, a Romberg task, a straight line walking task, a normal walking task, a turning on a spot task, a hopping on one foot task, a drawing squares with finger task, a drinking from a cup task, and a page-turning task.

The disease severity score may correspond to a plurality of disease severity sub-scores, and each disease severity sub-score may be indicative of one or more symptoms. The disease severity sub-score may be indicative of any of the symptoms described herein, and/or other symptoms not specifically described herein. For example, each disease severity sub-score may be indicative of one or more symptoms selected from: ataxia, truncal ataxia, gait ataxia, limb ataxia, spasticity, presence or absence of tremor, increased or decreased tremor, presence or absence of weakness, increased or decreased weakness, dysmetria, upper extremity motor dysfunction, increased or decreased dexterity, increased or decreased mobility, increased or decreased leg function, muscle wasting, muscle weakness, etc.

In another embodiment, method 1000 may include detecting a tremor in at least one portion of the digital representation of the human based on at least two of the motion descriptors. This may be accomplished by detecting acceleration and/or velocity of the human in the digital representation.

The disease which may be detected, assessed, evaluated, analyzed, quantified or recorded may be selected from multiple sclerosis, Huntington's disease, Parkinson's disease, Lou Gehrig's disease (ALS), and other diseases and/or conditions which affect movement and/or mobility.

The assessment of the one or more of the disease status and the disease severity may be based at least in part on one or more of: a previously determined disease status corresponding to the human digitally represented in the video data, and/or a previously determined disease severity corresponding to the human digitally represented in the video data.

Previously determined disease status and/or disease severity may be used to compare with currently assessed disease status and/or disease severity to determine improvement or regression of the human in the face of the disease or condition.

The video data depicts the human performing a physical movement indicative of the disease status and/or the disease severity. The physical movement includes one or more motor tasks described herein, or some other motor task known in the art. In a further embodiment, the video data may depict the human performing at least two of the motor tasks, in order to assess more than one aspect of the human's movement and/or mobility.

Each of the motion descriptors, in some approaches, represent an acceleration corresponding to a physical movement and/or a velocity corresponding to the physical movement. The physical movement is performed by the human digitally represented in the video data.

The velocity, in one embodiment, may be statistically indicative of a magnitude of the physical movement. The acceleration, i.e. temporal change in the direction and/or magnitude of the motion vectors, in one embodiment, may be indicative of jitter in the physical movement. The acceleration may refer to directionality change, which is acceleration in the sense of physics (change of a speed descriptor over time, e.g., movement with constant speed magnitude along a circle is movement with constant inward acceleration), but not in the colloquial sense (change of speed magnitude over time). Therefore, acceleration may refer to either definition of acceleration, in the sense of physics and in the colloquial sense, in various embodiments.

Each of the motion descriptors may represent a magnitude of a movement corresponding to one of the reference points. Magnitude may include a scalar motion descriptor of a type known in the art. In another embodiment, each of the motion descriptors may further represent a direction of the movement. Direction may include a vector motion descriptor of a type known in the art.

In preferred approaches, the presently disclosed disease status and/or severity assessment(s) may be based at least in part on image data exhibiting one or more discriminative spatio-temporal (DST) regions. As referred to herein, DST regions are portions of image data that are particularly informative for purposes of distinguishing patients exhibiting a particular symptom or condition from patients not exhibiting that particular symptom or condition. For example, and again with reference to multiple sclerosis (MS), patients suffering from relatively severe or advanced forms of MS are known to exhibit "intention tremor" upon targeted movements, for example when attempting to bring their phalanges in close physical proximity to their proboscis/mandible, while patients not suffering from MS exhibit no such tremor. As a result, for purposes of MS status and/or severity assessment, relying on a finger-to-nose test such as depicted in FIG. 2, a region substantially surrounding the patient's face may be considered a DST region.

Those having ordinary skill in the art reading the present descriptions will thus appreciate that a DST region is defined with respect to several factors. In general, the DST region is discriminative with respect to a particular disease status or severity (e.g., as opposed to being discriminative with respect to identity of different patients all exhibiting a common disease status or severity, discriminative with respect to a manner of acquiring a condition producing a common disease status or severity, etc.).

First, a DST region is primarily meaningful with respect to a particular disease or symptom. A region of a video particularly informative for distinguishing among categories of individuals with respect to one disease (disease status, disease severity score, etc.) may not necessarily be informative for distinguishing among categories of individuals with respect to other diseases. For instance, the facially-defined DST region discussed above with respect to MS and finger-to-nose tasks is uninformative (or even worse, misleading) when assessing extent of nerve damage to a burn patient by analyzing video of the patient attempting to walk on a treadmill.

Second, and similarly, a DST region is most meaningful with respect to a specific task being performed to assess the disease status and/or severity. Again, in the above example where a DST region includes the patient's face for purposes of assessing MS status/severity via a finger-to-nose test, the same region would not be discriminative for video depicting the patient performing a different task (e.g., page-turning, square-drawing, etc., as generally discussed herein and depicted in FIG. 2).

Third, those having ordinary skill in the art will also appreciate that the DST regions described herein are meaningful with further respect to time, i.e., the temporal portion of the video feed depicting the informative/meaningful information for disease status and/or severity discrimination. Again, considering the finger-to-nose test referenced above, the DST would not only be defined to encompass the patient's face and surrounding area, but also to coincide with those frame(s) of the video feed that depict the informative movement, e.g., the tremor. Temporal components of DST region definitions may be defined in any suitable manner, (e.g., identifying specific frames, identifying a timestamp or duration of video, etc.) and essentially indicate the most discriminative temporal region of the video data with respect to the disease status/severity under review.

As will be appreciated by skilled artisans upon reading the present descriptions, DST regions may thus be defined in any suitable manner to encompass information representing distinctive, discriminating characteristics between at least two disease status states (e.g., afflicted/not afflicted; chronic/acute; type I/type II; communicable/noncommunicable; etc.) and/or disease severity states (e.g., mild/moderate/severe/extreme; terminal; disease advancement state as indicated by a numerical score, etc.).

The presently disclosed inventive concepts also encompass the use of machine learning techniques, particularly support vector machine (SVM) techniques, and even more particularly one or more of a linear SVM and a Kernel SVM technique. Particularly, the present inventive concepts include the use of well-known SVM techniques applied to previously-unknown applications, e.g., finding DST regions within video data, and leveraging those DST regions in subsequent SVM analyses to discriminate between patient populations.

The presently-disclosed use of SVM principles enables disease assessment that is able to accomplish heretofore impossible fidelity and resolution. The exemplary technique may leverage one or more characteristic features of patients known to exhibit different disease status/severity to define "training sets" the support vector machine subsequently utilizes to define a hyperplane within the corresponding feature space. The hyperplane accurately and consistently distinguishes patients exhibiting one disease state from the other when subsequent data sets are evaluated with the goal of assessing disease status in a manner similar to the disease assessment performed when generating the training set(s).

Figure 11:
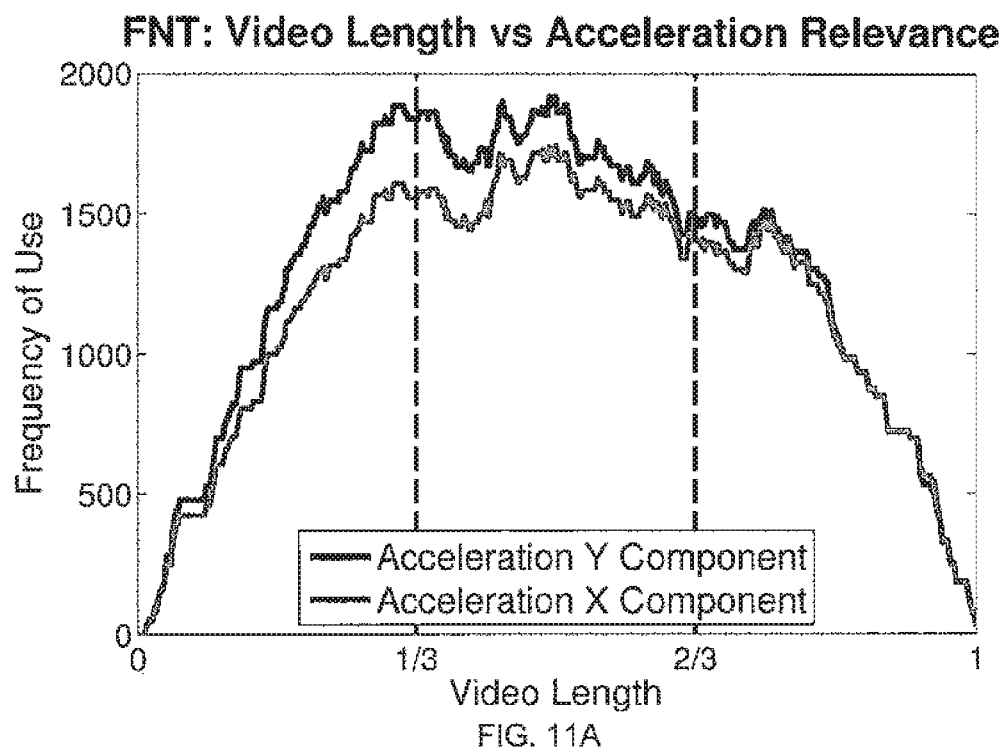
FIGS. 11A-11B show graphs of acceleration which illustrate discriminative spatio-temporal region learning, according to one embodiment.
Figure 11:
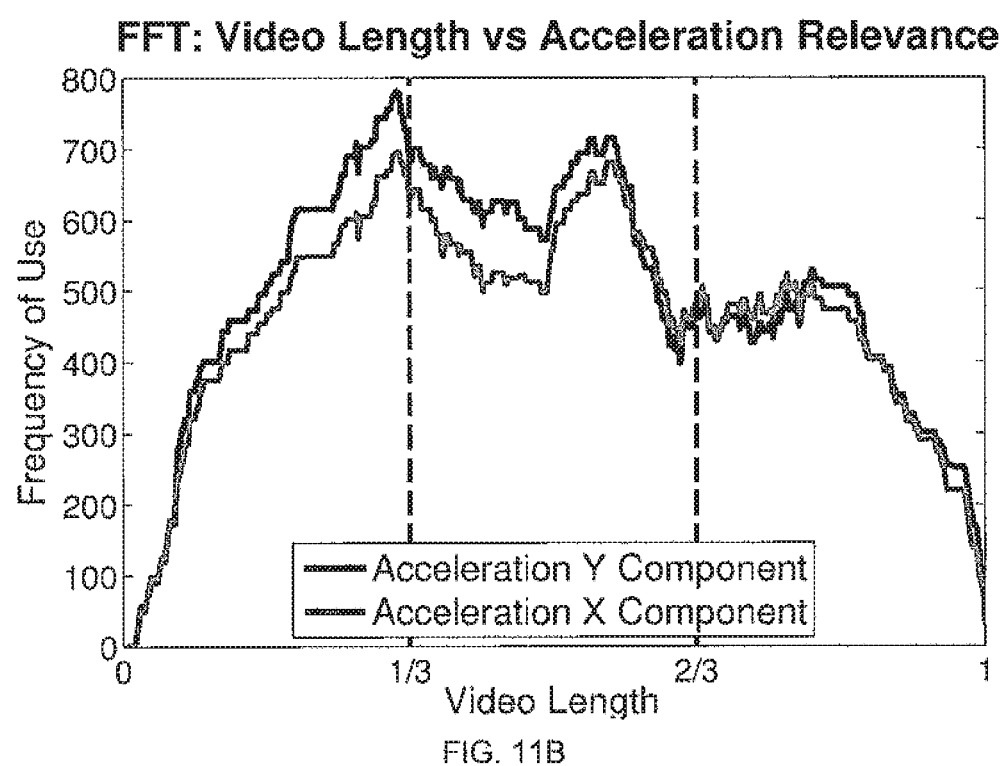

For example, in one approach disease status/severity is assessed utilizing a movement such as a tremor, shake, or jitter. A patient is video-recorded while performing a physical movement, and resulting video data are analyzed to determine frequency of movement direction reversal. While movement direction reversal may be indicated in any suitable manner, in preferred embodiments motion direction reversal is indicated by acceleration motion descriptors, and particularly preferably by at least two acceleration motion descriptors, one corresponding to a Y-component of motion and one to an X-component of motion. Each acceleration motion descriptor may be analyzed with respect to frequency of reversal as a function of time (i.e., temporal position in the video data), and this function may be plotted, substantially as shown in FIGS. 11A-11B.

The above, or a similarly-directed analysis may be performed on two patient populations: one exhibiting a particular disease status/severity characteristic, and the other not exhibiting the disease status/severity characteristic. Data from each population are synthesized to form "training sets" that, in aggregate, define one or more features uniquely associated with one of the patient populations (e.g., MS patients performing a finger-to-nose task distinctively exhibit a tremor in the facial DST region discussed above, while individuals not suffering from MS exhibit no such tremor. The SVM utilizes this distinguishing characteristic (represented at a much higher resolution in the form of specific quantitative acceleration motion descriptor data) to distinguish patients exhibiting the disease status/severity characteristic from those not exhibiting the status/severity characteristic.

In this manner, since the analysis is quantitative in nature and analyzes a much higher number of individual features than typically considered by a physician or neurologist evaluating a patient via one of the same tasks, patients may be provided with much higher resolution insight into the particular status/severity of their disease. Similarly, physicians and neurologists may track treatment outcome, patient satisfaction, or any other treatment-relevant information with respect to the higher-resolution of disease status/severity conditions, and evaluate existing treatment protocols as well as develop new treatment protocols leveraging the high-resolution data achievable only using a systematic approach to work with substantial datasets.

Clinically, the Kurtzke Expanded Disability Status Scale (EDSS) is a method of assessing and quantifying motion capability in neurological conditions such as multiple sclerosis. The EDSS is a manual (human assessed and scored) system. Several drawbacks are inherent in the EDSS. Foremost is that a trained neurologist is required to make the assessment. Over time, differences in rater judgment and neurological examinations can create inaccuracies. Limitations of categorization and human perception can also render condition progression tracking difficult. Daily fluctuations in patient performance may make a single visit assessment inaccurate.

Measures based on clinical judgment are of limited sensitivity due to the limited ability of humans to be able to make qualitative categorizations. Thus, when developing higher-sensitivity approaches for the same measure, the original measures cannot be used for validation.

The inventors, throughout the course of developing the inventive concepts generally presented herein into real-world applications, have generally observed that pairwise comparison of motor tasks (which may be indicative of disease status and/or disease severity) employing the presently-disclosed inventive concepts reveal robust intra-rater and inter-rater reliability.

Accordingly, embodiments of the invention provide a method or process whereby assessment reliability can be enhanced by presenting paired videos of subject motions. In one example, two patients performed identical motor tasks to a panel of "raters," which in this case were clinicians experienced in multiple sclerosis diagnostics, prognostics, and treatment. The clinicians were asked to identify whether the paired patients performed equally, or if not which of the patients performed worse (i.e., exhibited more severe symptoms) among the pair to provide a relative judgment of disease status/severity.

These relative clinician assessments were compared against disease status and/or disease severity assessments performed using the image analysis and machine learning-based techniques described herein. All results were analyzed with respect to "rater" identity to investigate inter- and intra-rater reliability, and results indicate high fidelity of the technique, even with respect to varying rater identity; i.e., quantitative values determined using the present methods were substantially consistent even when compared to ratings assigned to the same patient by a panel of clinical professionals. Specifically, comparitive disability gradings of the finger-to-nose (FNT) and drinking-from-cup (CUP) tests were significantly correlated with the coressponding Extended Disability Status Scale (EDSS) subscores.

Without intending to be bound to any particular theory, the inventors theorize these advantageous results may be explained as follows. Paired comparisons of video-captured defined movements of MS patients appear to reliably capture neurological judgment of motor dysfunction. As a benefit, it is possible to provide finer-grained (higher-resolution) differentiation, whereupon such fine gradings based on paired comparisons may serve as an improved external validation in the development of more sensitive (e.g., automated) outcome measures.

The method 1000 may be executed by a system, apparatus, or some other suitable device or component known in the art, such as one or more processors of a type known in the art, e.g., microprocessor, CPU, ASIC, FPGA, etc. In one such embodiment, an apparatus may comprise one or more processors and logic integrated with and/or executable by the one or more processors. The logic may be configured to receive video data comprising a plurality of frames, with at least two frames comprising a digital representation of a human; map a plurality of reference points for each of the at least two frames of the video data to the digital representation of the human in the at least two frames of the video data; calculate a plurality of motion descriptors for the at least two frames of the video data, with each motion descriptor corresponding to one of the reference points; and assess one or more of a disease status and a disease severity based on at least one of the motion descriptors.

In another embodiment, a computer program product may comprise a computer readable storage medium of a type known in the art. The computer readable storage medium may comprise computer readable program code configured to cause a processor, upon executing and/or reading the computer readable program code, to receive video data comprising a plurality of frames, with at least two frames comprising a digital representation of a human; map a plurality of reference points for each of the at least two frames of the video data to the digital representation of the human in the at least two frames of the video data; calculate a plurality of motion descriptors for the at least two frames of the video data, with each motion descriptor corresponding to one of the reference points; and assess one or more of a disease status and a disease severity based on at least one of the motion descriptors.

In one embodiment, the method 1000 of the present invention may be implemented with a personal portable apparatus such as a smart phone, tablet, watch or body-worn device, or other devices having sufficient video capture and computing capability.

Any of the various other embodiments described in relation to method 1000 may be implemented in the apparatus and/or the computer program product, as would be understood by one of skill in the art upon reading the present descriptions.

This example 1 defines an assessment tool that includes: a physical device that enables easy positioning of the depth-sensing camera, an interface that prompts the health professional in each step of the assessment, an instructional system to direct patients in movement performance, and a set of tools to support the health professional in managing the quality of the data. Thus, the recording tool comprises a patient-facing screen used to instruct patients in the neuro-assessment movements. Instructional videos are provided to guide the patient, as well as the health professional, in exactly how to perform the movement requested. They comprise simple line drawing animations accompanied by written and/or oral descriptions. A positioning screen provides a view of the depth image stream with centre crossbar to support precise positioning of the patient, and indicates whether the patient is an appropriate distance from the camera. There is an initial distractions screen which highlights any regions in the image that consistently report values of zero. Such regions are usually highly reflective surfaces that distort the infrared signal of the depth camera. It was found that the recording tool was acceptable both by health professionals and patients. Patients understood what to do with the recording tool, while health professionals found it easy to use.

In this example 2, a motor task analysis system as described in one or more embodiments herein was employed. Pre-defined movements from the standardized neurological assessment, covering upper and lower extremities and trunk, as well as movements typical of activities of daily living (ADL), were recorded in 72 MS patients and 102 healthy volunteers (HV). For all patients a standardized EDSS-assessment was performed and documented completely.

After segmentation of the recorded videos, information used for classification was extracted directly from the infrared depth sensor recordings, and used to train an automated image analysis algorithm according to embodiments of the present invention. The system is thus able to correctly classify patients according to the Neurostatus Subscores of the Finger to nose test: 0, 1 and 2, from the Cerebellar Functional System (Kappos et al). An ensemble-based machine learning algorithm was used to train the system.

Movements were classified by the machine learning algorithm into two classes: (1) asymptomatic (including both MS patients and HV) and (2) symptomatic concerning upper extremity tremor/dysmetria based on the standardized EDSS assessment Subscores of the cerebellar functional system.

Results are shown in Table 1 below:

TABLE 1

| | % correct classification | Sensitivity | Specificity |
|---|---|---|---|
| Asymptomatic vs. symptomatic upper extremity tremor/dysmetria | | | |
| FTN | 86.7 ± 3.2 | 78.3 ± 10.1 | 91.4 ± 2.2 |
| FTF | 89.8 ± 7.1 | 79.3 ± 17.4 | 91.1 ± 2.9 |
| DS | 90.2 ± 2.3 | 89.8 ± 7.1 | 90.3 ± 3.0 |
| Asymptomatic vs. symptomatic truncal ataxia | | | |
| TA | 85.1 ± 3.9 | 74.3 ± 11.9 | 86.8 ± 3.5 |

Where:
sensitivity = TP/(TP + FN) and specificity = FP/(FP + FN).
TP = true positive;
TN = true negative,
FN = false negative and
FP = false positive.
FTN = finger to nose;
FTF = finger to finger;
DS = drawing squares; and
TA = truncal ataxia.

Percentage of correct classification represents the proportion of recordings correctly predicted as either asymptomatic or symptomatic by the machine learning algorithm. True classification is based on standardized EDSS assessment.

The results showed that the system and method of the present invention enables an automated quantitative assessment of motor dysfunction in MS patients with useful sensitivity and specificity. The Example shows that the system and methods of the present invention allow reliable classifications of degrees of motor dysfunction, and that the algorithms employed herein provide information as to which components of subject's movements may be relevant for the clinical classification of the respective dysfunction.

Accordingly, embodiments of the invention provide an accuracy of classification of at least 85%, or 90%, or 95% or more. Embodiments of the invention provide a sensitivity of at least 75% or 80% or 85% or 90% or greater. Embodiments of the invention provide a specificity of at least 85% or 90% or 95% or more.

In an example 3 there is provided a computer-implemented method comprising:

receiving a video depicting at least part of a person or animal performing a motor task;

inputting the video to a trained machine learning system, having been trained to find location-dependent local motion features of videos which discriminate between a plurality of classes of the motor task; and receiving, from the trained machine learning system, data about which of the plurality of classes the motor task is predicted to belong to.

In this way motor tasks performed by people can be analyzed and assessed in an accurate, repeatable manner which is automated and so objective.

In many examples the local motion features comprise velocity or acceleration features. These types of features may be computed accurately and efficiently and may be computed in advance of machine learning training and test phases. This improves the quality of the motor task data obtained from the machine learning system and the speed of obtaining that data.

In many examples the above methods comprise calculating, for pairs of frames of the video, motion descriptors, and wherein inputting the video to the trained machine learning system comprises inputting the motion descriptors.

For example the motion descriptors are optical flow values. Where optical flow values are used the resulting system is found to be very robust to noise or errors in the videos.

In some examples the above methods comprise, at the machine learning system, calculating the local motion features using a plurality of the motion descriptors. For example, by taking into account motion descriptors in at least one sub-volume of the video. For example, calculating the local motion features by taking into account motion descriptors in two sub-volumes of the video. For example, calculating the local motion features by taking into account differences between motion descriptors in the sub-volumes of the video. Using sub-volumes of videos in these ways is found particularly effective in discriminating between motor task classes.

Some examples comprise calculating the acceleration features by taking into account frequency of change of direction of rate of change of the optical flow values of a sub-volume of the video. Using a directional acceleration feature is found very effective in discriminating between motor task classes.

Some examples comprise disregarding changes of direction of the rate of change of the optical flow values, where the magnitude of the optical flow is below a threshold. This helps to distinguish between motion due to noise and actual motion of the person.

Some examples comprise pre-processing the video prior to inputting the video to the trained machine learning system, by scaling, centering and carrying out foreground extraction. This simplifies the use of the trained machine learning system at test time and reduces the test time processing duration.

In some examples the video is of any length, and the local motion features are calculated in a manner which takes into account the length of the video. This is very useful where the motor tasks exhibit large variability in duration between individuals.

Some examples comprise training the machine learning system using videos of people performing a motor task, where the videos are labeled with labels indicating which of a plurality of possible classes the motor task belongs to, and where the videos are of different lengths.

Many examples may comprise inputting the video to a trained machine learning system comprising any of: a random decision forest, a jungle of directed acyclic graphs, an ensemble of support vector machines such as a linear SVM, a Kernel SVM, etc., as would be understood by one having ordinary skill in the art upon reading the present descriptions.

Some examples comprise inputting the video to a trained machine learning system comprising an ensemble of support vector machines, each support vector machine being a split node of a binary decision tree. This gives a practical way of using support vector machines despite the high and variable number of dimensions of the video data.

Some examples comprise inputting the video to a trained machine learning system comprising an ensemble of support vector machines, individual ones of the support vector machines having been trained using fixed length feature descriptors comprising randomized location-dependent local motion features computed from labeled training videos. The resulting ensemble of support vector machines may be referred to as a randomized ensemble of support vector machines.

An example 4 provides a motor-task classifier comprising: a memory storing a video depicting at least part of a person or animal performing a motor task; a trained machine learning system, having been trained to find location-dependent local motion features of videos which discriminate between a plurality of classes of the motor task; and a processor arranged to compute motion descriptors from the video, apply the motion descriptors to the trained machine learning system, and to receive in response, data about which of the plurality of classes to which the motor task is predicted to belong.

An example 5 comprises: receiving video data comprising a plurality of frames, at least two frames comprising a digital representation of a human; mapping a plurality of reference points for each of the at least two frames of the video data to the digital representation of the human in the at least two frames of the video data; calculating a plurality of motion descriptors for the at least two frames of the video data, each motion descriptor corresponding to one of the reference points; and assessing one or more of a disease status and a disease severity based on at least one of the motion descriptors.

For example, the video data comprises optical flow information.

In an example the at least two frames of the video data are shifted temporally from one another, and at least a portion of the digital representation of the human is spatially shifted among the at least two frames of the video data.

For example, the video data comprises non-contact active three-dimensional (3D) scan information.

For example each of the at least two frames of the video data is a 16-bit grayscale image, and wherein each pixel is characterized by a brightness value in a range represented by 0-65,536.

For example the method further comprises calculating a disease severity score based on at least one of the motion descriptors, wherein the disease severity is assessed based at least in part on the disease severity score.

For example, the disease severity score has a value in a range from about 0.0 to about 12.0.

In an example the disease severity score is based at least in part on a plurality of disease severity sub-scores, each of the disease severity sub-scores corresponding to a motor task selected from:
  a truncal ataxia task;
  a finger-to-nose task;
  a finger-to-finger task;
  a Romberg task;
  a straight line walking task;
  a normal walking task;
  a turning on a spot task;
  a hopping on one foot task;
  a drawing squares with finger task;
  a drinking from a cup task; and
  a page-turning task.

In an example the disease severity score corresponds to a plurality of disease severity sub-scores, and wherein each disease severity sub-score is indicative of one or more symptoms selected from:
  ataxia;
  truncal ataxia;
  gait ataxia;
  limb ataxia;
  spasticity;
  tremor;
  weakness;
  dysmetria;
  upper extremity motor dysfunction;
  dexterity;

mobility; and
leg function.

An example further comprises detecting a tremor in at least one portion of the digital representation of the human based on at least two of the motion descriptors.

In an example the disease is selected from: multiple sclerosis, Huntington's disease, and Parkinson's disease.

In various examples, the assessing is further based at least in part on one or more of: a previously determined disease status corresponding to the human digitally represented in the video data; and a previously determined disease severity corresponding to the human digitally represented in the video data.

In an example the video data depicts the human performing a physical movement indicative of at least one of: the disease status and the disease severity.

In an example the physical movement comprises one or more motor tasks selected from:
a truncal ataxia task;
a finger-to-nose task;
a finger-to-finger task;
a Romberg task;
a straight line walking task;
a normal walking task;
a turning on a spot task;
a hopping on one foot task;
a drawing squares with finger task;
a drinking from a cup task; and
a page-turning task.

In the example above the video data may depict the human performing at least two of the motor tasks.

In an example each of the motion descriptors represents one or more of: an acceleration corresponding to a physical movement; and a velocity corresponding to the physical movement, and wherein the physical movement is performed by the human digitally represented in the video data.

In an example the velocity is statistically indicative of a magnitude of the physical movement.

In an example the acceleration is indicative of jitter in the physical movement.

In an example each of the motion descriptors represents a magnitude of a movement corresponding to one of the reference points.

In an example each of the motion descriptors further represents a direction of the movement.

In embodiments of the invention, the motor task analysis system and/or components thereof are used in conjunction with a therapy for a disease, state or condition. Hence, evaluation or progress monitoring of a disease, state or condition can be assisted by the motor task analysis system and/or components thereof. For example, embodiments of the invention are used to evaluate patients or subjects who have, or were suspected of having a neurological disease or condition such as multiple sclerosis, Parkinson's etc. Accordingly, embodiments of the invention are contemplated wherein the motor task analysis system is used to periodically monitor, assess and evaluate a patient's physical movement, before, during and after a course of therapy.

The therapy may comprise administration of immunomodulating drugs, such as interferon beta-1b, or S1P receptor agonists, such as fingolimod, siponimod or 2-Amino-2-[2-[4-[3-(benzyloxy)phenylsulfanyl]-2-chlorophenyl]ethyl]propane-1,3-diol hydrochloride. A Parkinson's disease therapy may comprise administration of drugs selected from the group of levodopa, carbidopa, and entacapone. Preferably, said Parkinson's disease therapy comprises the combination of levodopa, carbidopa, and entacapone.

A number of drugs are available for the treatment of motor diseases and may be selected from the classes of immunomodulating drugs and S1P receptor agonists. Other diseases, as noted herein, such as muscle wasting and muscle weakness may be treated by the following classes of drugs: myostatin antagonist, such as an anti-ActRII receptor antibody, such as bimagrumab.

Embodiments of the invention accordingly comprise a kit comprising the motor task analysis system embodied in software which may be installed in a hospital or clinician's computing system, together with an appropriate drug for therapy, such as Fingolimod. The kit comprising the software and drug therapy may also additionally comprise an appropriate video capture system, such as a Microsoft Kinect system.

Embodiments of the motor task analysis system may comprise software which may be installed, such as via an app store, on a personal smartphone or portable computing device, together with instructions for use.

Embodiments of the invention comprise a method of using the motor task analysis system described herein to enable drug development researchers to better, assess, refine, monitor, quantify or evaluate drugs under development (including existing drugs and evaluated for new indications) for diseases and conditions, which diseases and conditions result in some manifestation in patient motor function, or change in motor function.

There is further provided: a trained machine learning system having been trained to find location-dependent local motion features of videos which discriminate between a plurality of classes of the motor task, wherein the video depicts at least part of a person or animal performing a disease or condition relevant motor task, and wherein said video is inputted to said trained machine learning system, and wherein said trained machine learning system delivers data about which of the plurality of classes the motor task is predicted to belong to.

There is further provided: fingolimod for use in the treatment of multiple sclerosis, wherein said treatment comprises the computer-implemented method according to any of claims 1-17.

There is further provided: siponimod for use in the treatment of multiple sclerosis, wherein said treatment comprises the computer-implemented method according to any of claims 1-17.

There is further provided: levodopa for use in the treatment of multiple sclerosis, wherein said treatment comprises the computer-implemented method according to any of claims 1-17.

There is further provided: bimagrumab for use in the treatment of multiple sclerosis, wherein said treatment comprises the computer-implemented method according to any of claims 1-17.

There is further provided: 2-Amino-2-[2-[4-[3-(benzyloxy)phenylsulfanyl]-2-chlorophenyl]ethyl]propane-1,3-diol hydrochloride for use in the treatment of multiple sclerosis, wherein said treatment comprises the computer-implemented method according to any of claims 1-17.

The term 'computer' or 'computing-based device' is used herein to refer to any device with processing capability such that it can execute instructions. Those skilled in the art will realize that such processing capabilities are incorporated into many different devices and therefore the terms 'computer' and 'computing-based device' each include PCs, servers, mobile telephones (including smart phones), tablet computers, set-top boxes, media players, games consoles, personal digital assistants and many other devices.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible storage media include computer storage devices comprising computer-readable media such as disks, thumb drives, memory etc and do not include propagated signals. Propagated signals may be present in a tangible storage media, but propagated signals per se are not examples of tangible storage media. The software can be suitable for execution on a parallel processor or a serial processor such that the method steps may be carried out in any suitable order, or simultaneously.

This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

The term 'subset' is used herein to refer to a proper subset such that a subset of a set does not comprise all the elements of the set (i.e. at least one of the elements of the set is missing from the subset).

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. A computer-implemented method comprising:
   providing a machine learning system;
   training the machine learning system using a plurality of individuals to find location-dependent local motion features of videos which discriminate between a plurality of classes of motor tasks, the location-dependent local motion features including data relating to one or more discriminative spatio-temporal regions;
   receiving a video depicting at least part of a person or animal performing at least one of the motor tasks and including data relating to one or more discriminative spatio-temporal regions of the video;
   inputting the video to the trained machine learning system;
   receiving, from the trained machine learning system, data about which of the plurality of classes of motor tasks the at least one motor task is predicted to belong to; and
   evaluating a neurological disease or condition of the person or animal performing the at least one of the motor tasks based on the received data including data relating to the one or more discriminative spatio-temporal regions of the video.

2. A method as claimed in claim 1 wherein the local motion features comprise velocity or acceleration features.

3. A method as claimed in claim 2 comprising calculating the acceleration features by taking into account frequency of change of direction or rate of change of optical flow values of a sub-volume of the video.

4. A method as claimed in claim 3 comprising disregarding changes of direction of the rate of change of the optical flow values, where a magnitude of the optical flow values is below a threshold.

5. A method as claimed in claim 1 comprising calculating, for pairs of frames of the video, motion descriptors, and wherein inputting the video to the trained machine learning system comprises inputting the motion descriptors.

6. A method as claimed in claim 1 comprising pre-processing the video prior to inputting the video to the trained machine learning system, by scaling, centering and carrying out foreground extraction.

7. A method as claimed in claim 1 comprising training the machine learning system using videos of people performing the at least one of the motor tasks, where the videos are labeled with labels indicating which of the plurality of possible classes the at least one of the motor tasks belongs to, and where the videos are of different lengths.

8. A method as claimed in claim 1 comprising inputting the video to a trained machine learning system comprising any of a random decision forest, a jungle of directed acyclic graphs, an ensemble of support vector machines.

9. A method as claimed in claim 1, wherein the neurological disease or condition of the person or animal performing the at least one of the motor tasks comprises one or more of Parkinson's Disease, Huntington's disease, Amyotrophic Lateral Sclerosis (ALS), cerebral palsy, Rheumatoid Arthritis, muscle wasting, chronic obstructive pulmonary disease (COPD), autism, schizophrenia, Alzheimer's disease, tremors, multiple sclerosis, depression, dementia, mania, bipolar disorder, obsessive-compulsive disorder, congestive heart failure, cardiac arrhythmia, gastrointestinal disorder, and incontinence.

10. A computer-implemented method comprising:
providing a machine learning system;
training the machine learning system using a plurality of individuals to find location-dependent local motion features of videos which discriminate between a plurality of classes of motor tasks, the location-dependent local motion features including data relating to one or more discriminative spatio-temporal regions;
receiving a video depicting at least part of a person or animal performing at least one of the motor tasks and including data relating to one or more discriminative spatio-temporal regions of the video;
inputting the video to the trained machine learning system;
receiving, from the trained machine learning system, data about which of the plurality of classes of motor tasks the at least one motor task is predicted to belong to; and
evaluating a neurological disease or condition of the person or animal performing the at least one of the motor tasks based on the received data including data relating to the one or more discriminative spatio-temporal regions of the video,
wherein the machine learning system is trained using videos of people performing the at least one of the motor tasks, where the videos are labeled with labels indicating which of the plurality of possible classes the at least one of the motor tasks belongs to.

11. A method as claimed in claim 10 wherein the local motion features comprise velocity or acceleration features.

12. A method as claimed in claim 11 comprising calculating the acceleration features by taking into account frequency of change of direction or rate of change of optical flow values of a sub-volume of the video.

13. A method as claimed in claim 12 comprising disregarding changes of direction of the rate of change of the optical flow values, where a magnitude of the optical flow values is below a threshold.

14. A method as claimed in claim 10 comprising calculating, for pairs of frames of the video, motion descriptors, and wherein inputting the video to the trained machine learning system comprises inputting the motion descriptors.

15. A method as claimed in claim 10 comprising pre-processing the video prior to inputting the video to the trained machine learning system, by scaling, centering and carrying out foreground extraction.

16. A method as claimed in claim 10 wherein the videos of people performing the at least one of the motor tasks are of different lengths.

17. A method as claimed in claim 10 comprising inputting the video to a trained machine learning system comprising any of a random decision forest, a jungle of directed acyclic graphs, an ensemble of support vector machines.

18. A method as claimed in claim 10, wherein the neurological disease or condition of the person or animal performing the at least one of the motor tasks comprises one or more of Parkinson's Disease, Huntington's disease, Amyotrophic Lateral Sclerosis (ALS), cerebral palsy, Rheumatoid Arthritis, muscle wasting, chronic obstructive pulmonary disease (COPD), autism, schizophrenia, Alzheimer's disease, tremors, multiple sclerosis, depression, dementia, mania, bipolar disorder, obsessive-compulsive disorder, congestive heart failure, cardiac arrhythmia, gastrointestinal disorder, and incontinence.

* * * * *